Figure 1:
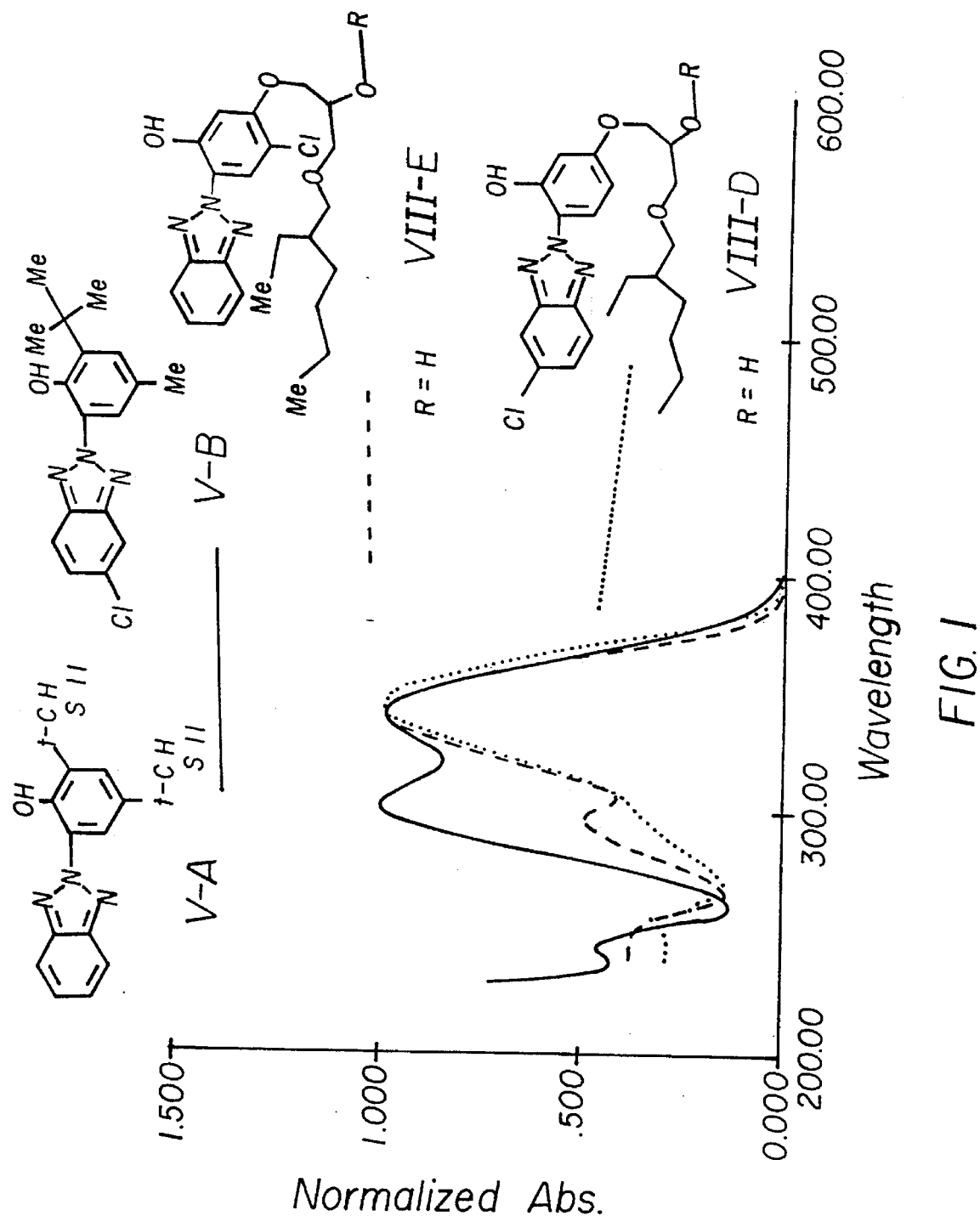

United States Patent [19]
Vishwakarma et al.

[11] Patent Number: 5,585,228
[45] Date of Patent: Dec. 17, 1996

[54] BENZOTRIAZOLE BASED UV ABSORBING COMPOUNDS AND PHOTOGRAPHIC ELEMENTS CONTAINING THEM

[75] Inventors: Lal C. Vishwakarma; Glenn M. Brown, both of Rochester, N.Y.

[73] Assignee: Eastman Kodak Company, Rochester, N.Y.

[21] Appl. No.: 473,592

[22] Filed: Jun. 7, 1995

Related U.S. Application Data

[63] Continuation-in-part of Ser. No. 346,717, Nov. 30, 1994, abandoned.

[51] Int. Cl.$^6$ .................................................. G03C 1/815
[52] U.S. Cl. .................. 430/512; 252/589; 430/931; 524/91; 548/260
[58] Field of Search ........................... 430/512, 931; 548/260; 524/91; 252/589

[56] References Cited

U.S. PATENT DOCUMENTS

| | | | |
|---|---|---|---|
| 4,028,331 | 6/1977 | Hotta et al. | 260/45.8 |
| 4,220,711 | 9/1980 | Nakamura et al. | 430/507 |
| 4,414,393 | 11/1983 | Dexter et al. | 548/260 |
| 4,518,686 | 5/1985 | Sasaki et al. | 430/512 |
| 4,587,346 | 5/1986 | Winter et al. | 54/260 |
| 4,692,399 | 9/1987 | Sasaki et al. | 430/507 |
| 4,716,234 | 12/1987 | Dunks et al. | 548/260 |
| 4,803,254 | 2/1987 | Dunks et al. | 548/260 |
| 4,853,471 | 8/1989 | Rody et al. | 548/261 |
| 4,865,957 | 9/1989 | Sakai et al. | 430/505 |
| 4,973,701 | 11/1990 | Winter et al. | 548/260 |
| 4,975,360 | 12/1990 | Sasaki et al. | 430/512 |
| 4,992,358 | 2/1991 | Sasaki et al. | 430/512 |
| 5,095,062 | 3/1992 | Winter et al. | 524/91 |
| 5,099,027 | 2/1992 | Vogl et al. | 548/260 |
| 5,112,728 | 5/1992 | Tanji et al. | 430/507 |

FOREIGN PATENT DOCUMENTS

| | | |
|---|---|---|
| 2487994 | 2/1982 | France . |
| 48-35376 | 8/1969 | Japan . |
| 63-264748 | 11/1988 | Japan . |
| 63-311354 | 12/1988 | Japan . |
| 01282541 | 11/1989 | Japan . |
| 2-37343 | 2/1990 | Japan . |
| 03139589 | 6/1991 | Japan . |

*Primary Examiner*—Richard L. Schilling
*Attorney, Agent, or Firm*—Edith A. Rice

[57] ABSTRACT

Ultraviolet absorbing compounds of formula (I) and photographic elements containing such compounds:

(I) a benzotriazole-phenol structure with substituent $O-R_4-O-(L)_p-A^*$ wherein:
$R_4$ is a bivalent linking group; the benzo or phenyl ring shown may be further substituted or unsubstituted;
L is a bivalent linking group;
p is 0 or 1;
$A^*$ is an alkyl group having an asymmetric carbon or silicon atom, and;
wherein the ultraviolet absorbing compound of formula (I) is a mixture of two enantiomers about the asymmetric carbon or silicon of $A^*$.

29 Claims, 3 Drawing Sheets

BENZOTRIAZOLE BASED UV ABSORBING COMPOUNDS AND PHOTOGRAPHIC ELEMENTS CONTAINING THEM

CROSS-REFERENCE TO RELATED APPLICATIONS

This application is a continuation-in-part of application Ser. No. 08/346,717 for BENZOTRIAZOLE BASED UV ABSORBING COMPOUNDS AND PHOTOGRAPHIC ELEMENTS CONTAINING THEM, filed Nov. 30, 1994 by Vishwakarma and Brown, now abandoned. The foregoing application is incorporated herein by reference.

FIELD OF THE INVENTION

This invention relates to particular benzotriazole based UV absorbing compounds, and to photographic elements containing such compounds.

BACKGROUND

Typical photographic elements use silver halide emulsions, the silver halide having a native sensitivity to ultraviolet radiation. Ultraviolet radiation ("UV") as used in this application means light having a wavelength of 300–400 nm. Such UV sensitivity is usually undesirable in that it produces an image on the photographic element which is not visible to the human eye. Furthermore, the image dyes in the color photographs are known to fade due to action of UV light. Also other organic molecules such as unused color forming couplers in the emulsion layers and optical brighteners in the paper support degrade due to action of UV light and generate undesirable color stains on the finished photographs. Therefore, photographic elements typically contain a UV absorbing compound (sometimes referred to simply as a "UV absorber"). Another function of UV absorbers is to prevent the formation of undesirable patterns caused by electrostatic discharge in silver halide photographic materials. In general, UV absorbers impart light stability to organic molecules in various products which are susceptible to degrade as a result of the action of UV.

Generally, an effective UV absorber should have its peak absorption above a wavelength of 320 nm. The absorption peak may be at a longer wavelength, as long as absorption drops off sufficiently as it approaches the visual range (approximately 400 to 700 nm) so that no visible color is shown by the compound. In addition, to be effective, a UV absorber should have a high extinction coefficient in the desired wavelength range. However, for the most desirable UV protection, the high extinction coefficient should be at those wavelengths sufficiently below the visual range so that the compound should not be visually yellow.

UV absorbers of the benzotriazole class for photographic and other applications are well known. They include hydroxyphenyl benzotriazoles with various substituents on the hydroxyphenyl ring, including alkoxy. Compounds of the foregoing type are disclosed, for example, in Japanese published patent application JP 3139589. U.S. Pat. No. 5,112,728 discloses photographic elements with liquid hydroxyphenyl benzotriazole UV absorbers, including one example which incidentally has a racemic carbon center. Also, U.S. Pat. Nos. 4,975,360; 4,973,701 and 4,996,326 all disclose photographic elements which contain liquid hydroxyphenyl benzotriazoles as UV absorbers. U.S. Pat. Nos. 4,973,701 and 4,992,358 discuss various advantages of the absorbers being liquid. Some of the compounds in those patents include substituents on the hydroxyphenyl ring which incidentally have a racemic carbon center.

European Patent Application 0 451 813 and published Japanese Patent Application JP 04316563, disclose a photographic element containing hydroxyphenyl benzotriazoles of Formula (II):

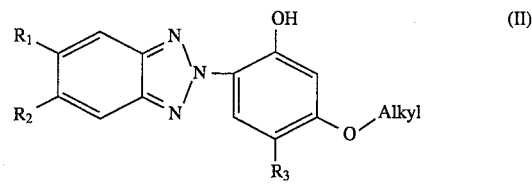

In formula (II) the alkyl group may be branched. A number of compounds shown in those Applications have a racemic carbon center. Another EP 0 571 935 mentioned alkoxy substituents in the phenol ring but with no specific substitution at the 4'-position in Formula (II). Moreover, the compounds of Formula (II) have been reported in the literature by M. Karvas and J. Holcik., *Chemicky Prumysl*, 17 (1), 543 (1967); and in *Chemical Abstract* 70 (12): 48169j (1969). However, as shown later, the intrinsic light stability of one of the representative compounds (III) (formula below) from those references is relatively poor.

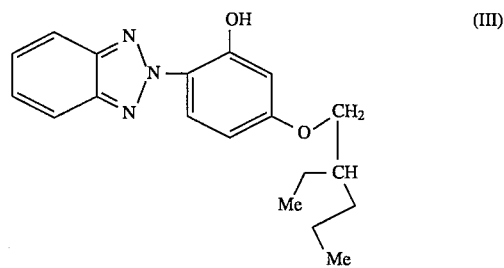

UV absorbers which are currently used in photographic products include those of formula (V-A) and (V-B) below:

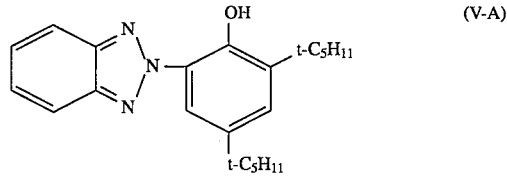

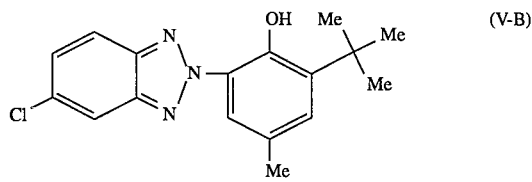

However, compounds (V-A) and (V-B) have a propensity to crystallize out during cold storage of a dispersion of them.

It is therefore desirable to have other UV absorbing compounds suitable for photographic uses, which are relatively stable in a photographic environment, do not tend to crystallize out at ordinary temperatures at which photographic elements are used and/or stored, and which have a high extinction coefficient so that less of it needs to be used to obtain the same UV absorption.

SUMMARY OF THE INVENTION

The present invention therefore provides UV absorbing compounds of formula (I), and photographic elements containing them:

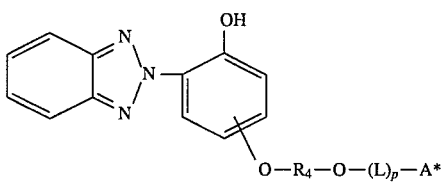

(I)

wherein:

R$_4$ is a bivalent linking group; the benzo or phenyl ring shown may be further substituted or unsubstituted;

L is a bivalent linking group;

p is 0 or 1;

A* is an alkyl group having an asymmetric carbon or silicon atom, and;

wherein the ultraviolet absorbing compound of formula (I) is a mixture of two enantiomers about the asymmetric carbon or silicon of A*.

The ultraviolet absorbing compound of formula (I) preferably have a 40/60 to 60/40 (preferably a 50/50 mixture) mixture of two enantiomers.

UV absorbing compounds of formula (I) can have a wavelength of maximum absorption ("λmax") which is desirably in the longer UV region (336–350 nm), have a sharp dropping absorption profile at wavelengths slightly shorter than 400 nm making them useful with known fluorescent brighteners, are relatively stable in the environment of a photographic element, have a low tendency to crystallize in photographic elements, and have high extinction coefficients.

DRAWINGS

Figure 2:
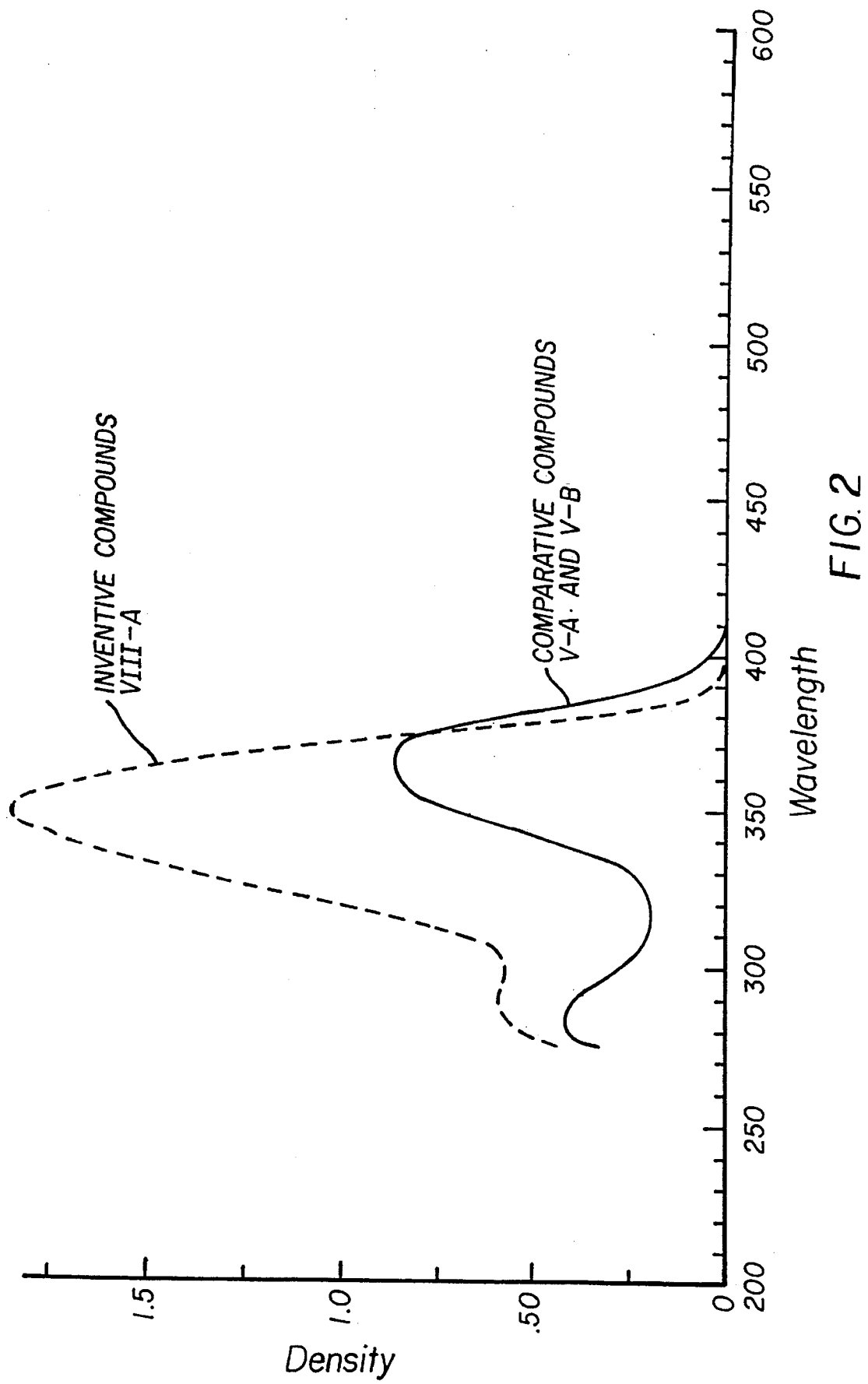
Figure 3:
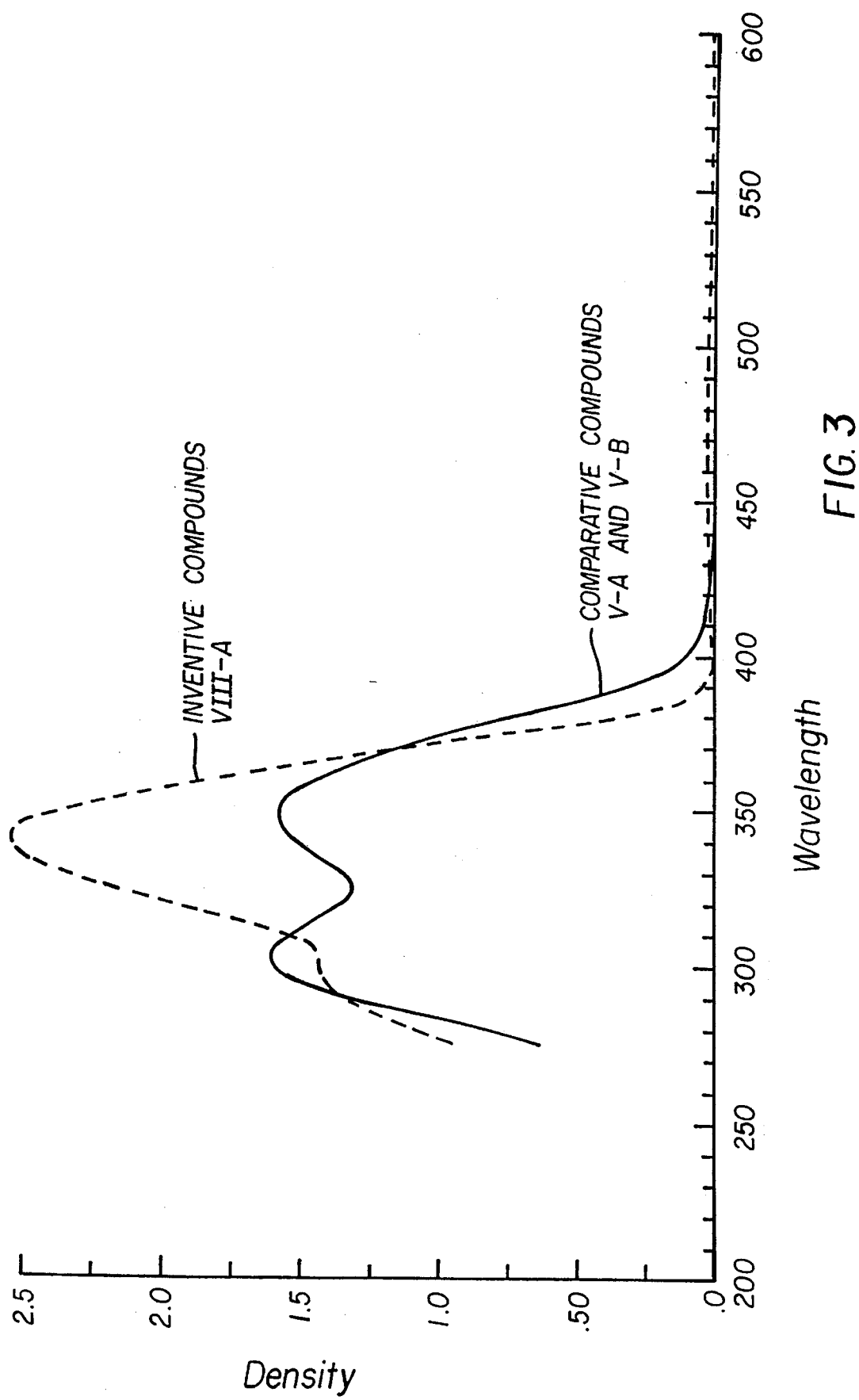

FIG. 1 represents normalized absorption spectra in solution of UV absorbing compounds of the present invention and comparative compounds; and FIGS. 2 and 3 are absorption spectra of coatings in photographic element of inventive compound VIII-A and comparative compounds V-A and V-B in total transmission and specular modes respectively, as described below.

EMBODIMENTS OF THE INVENTION

In the present application, reference to ultraviolet or UV in relation to the present invention refers to the wavelength range of 300 to 400 nm unless the contrary is indicated. Additionally, reference to "under", "above", "below", "upper", "lower" or the like terms in relation to layer structure of a photographic element, is meant the relative position in relation to light when the element is exposed in a normal manner. "Above" or "upper" would mean closer to the light source when the element is exposed normally, while "below" or "lower" would mean further from the light source. Since a typical photographic element has the various layers coated on a support, "above" or "upper" would mean further from the support, while "below" or "under" would mean closer to the support. Further, reference to any chemical "group" (such as alkyl group, aryl group, heteroaryl group, and the like) includes the possibility of it being both substituted or unsubstituted (for example, alkyl group and aryl group include substituted and unsubstituted alkyl and substituted and unsubstituted aryl, respectively). Generally, unless otherwise specifically stated, substituent groups usable on molecules herein include any groups, whether substituted or unsubstituted, which do not destroy properties necessary for the photographic utility. It will also be understood throughout this application that reference to a compound of a particular general formula includes those compounds of other more specific formula which specific formula falls within the general formula definition, unless otherwise indicated.

As is well known, enantiomers have identical structural formulas except they are non-superimposable mirror images of one another. Further, in reference to enantiomeric mixtures, proportions are in mole ratios.

Compounds of formula (I) preferably are of the following formula:

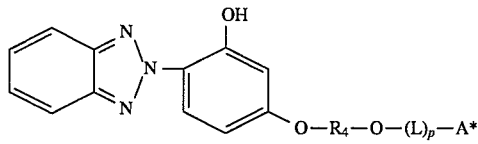

In compounds of formula (I), p may particularly be 1 while L is an alkylene group having a chain extending between the O shown and A* of 1 to 4 carbon atoms in length. Compounds of formula (I) are preferably of formula (IA) below:

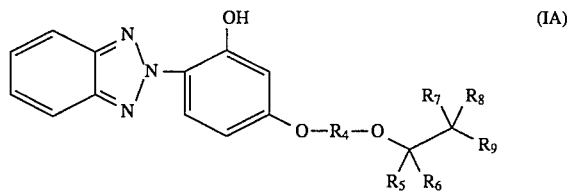

(IA)

wherein:

R$_4$ is a bivalent linking group in which the atoms of the chain extending between the two oxygen atoms shown are preferably all saturated;

R$_5$ and R$_6$, together with the carbon atom to which they are attached, forms a carbonyl group or they are, independently, H or substituents, and the benzo or phenyl ring shown may be further substituted or unsubstituted;

R$_7$, R$_8$ and R$_9$ are, independently: H; halogen; cyano; a 1 to 18 carbon alkyl group or alkoxy group either of which may have 1 to 5 intervening oxygen, sulfur or nitrogen atoms; 6 to 20 carbon aryl group or aryloxy group; or a heteroaromatic group in which the aromatic ring has 1 to 3 heteroatoms selected from N, S and O; and provided that R$_7$, R$_8$, and R$_9$ are selected such that the carbon atom to which they are attached is asymmetric.

In compounds of formula (I) (which includes formula (IA) compounds), the bivalent linking group R$_4$ may, for example, be an alkylene group having a chain of 2 to 20 atoms in length, with or without intervening oxygen, sulfur or nitrogen atoms. However, as already pointed out the atoms of the chain extending between the two oxygen atoms shown are preferably all saturated. This means that none of the atoms in the chain extending between the two oxygen atoms shown, would have any type of double bond. Thus, R$_4$ cannot have atoms in the chain such as —C=C— or carbonyl groups. However, this does not exclude the possibility of R$_4$ having unsaturated atoms which are not in the chain extending between the two oxygen atoms shown. For example, R$_4$ in this situation could not be a group such as (A) below (since it has an unsaturated carbon in the chain of atoms extending between the two oxygen atoms shown in formula (I), namely the carbon of the carbonyl group), but could be a group such as (B) below (since the unsaturated carbon is not in the chain of atoms extending between the two oxygen atoms shown in formula (I)):

$$-(CH_2)_2-\underset{\underset{O}{\|}}{C}-  \qquad (A)$$

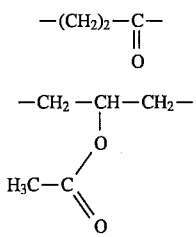
(B)

More particularly, $R_4$ may particularly have from 1 to 20 carbon atoms (or 1 to 10, 1 to 6, or 1 to 3 carbon atoms). $R_4$ may particularly be an alkylene group. $R_4$ may be unsubstituted or substituted with, for example, a 1 to 10 carbon alkoxy (or 1 to 6, or 1 to 2 carbon alkoxy), a 1 to 10 carbon atom alkyl sulfide (or 1 to 6, or 1 to 2 carbon alkyl sulfide), 0 to 10 carbon amino (or 0 to 6, or 0 to 2 carbon amino), or halogen. As already described, $R_4$ may contain intervening oxygen, sulfur or nitrogen atoms, such as 1 to 5 atoms of any of the foregoing type (or 1 to 2 such intervening atoms). By $R_4$ being substituted includes the possibility of the substituents forming a ring. For example, $R_4$ could then include an alicyclic or heterocylic ring (such as a 3 to 10 or 4, 5, or 6, membered ring). When the ring is heterocyclic it may contain, for example, have 1, 2, or 3 heteroatoms (which may be the same or different) selected from O, S or N. Examples of such rings as part of $R_4$ preferably include cyclohexyl, pyrrolidinyl, tetrahydrofuranyl, tetrahydrothienyl or piperidinyl, although less preferably benzo, pyrrolo furyl, thienyl or pyridyl rings could be present. $R_4$ may include as a substituent, particularly when $R_4$ is an alkylene group as described (that is with or without the intervening heteroatoms described), an ether or ester containing group. Particularly, the ether or ester containing substituent in $R_4$ may be of the formula $R_{10}-O-(R_{11})_n-$ or $R_{10}C(O)O-(R_{11})_n^-$, where $R_{10}$ and $R_{11}$ are, independently, an alkyl group and n is 0 or 1. $R_{11}$ may have, for example, 1 to 6 carbon atoms, while $R_{10}$ may have, for example, 1 to 20 carbon atoms (for example, 1 to 10, or 6 to 10).

Examples of $R_4$ include the following:

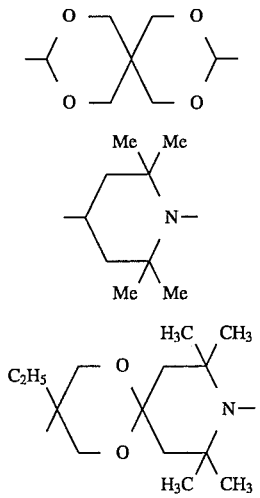

The benzo ring and the hydroxy substituted phenyl ring may each be further substituted. For example, either may have 1 to 4 further substituents. Substituents may, for example, independently be, 1 to 18 carbon alkyl (or 1 to 6, or 1 to 2 carbon alkyl), aryl (such as 6 to 20 carbon atoms), heteroaryl (such as pyrrolo, furyl or thienyl), aryloxy (such as 6 to 20 carbon atoms) alkoxy (such as 1 to 6 or 1 to 2 carbon alkoxy), cyano, or halogen (for example F or Cl, particularly having Cl on the benzo ring at the 5 and/or 6 position, and/or on the hydroxy substituted phenyl at the 5' positon). Substituents for the benzo ring can also include ring fused thereto, such as a benzo, pyrrolo, furyl or thienyl ring. Any of the alkyl and alkoxy substituents may have from 1 to 5 (or 1 to 2) intervening oxygen, sulfur or nitrogen atoms.

As already descirbed, $R_5$ and $R_6$, together with the carbon atom to which they are attached, forms a carbonyl group or they are, independently, H or substituents. When $R_5$ or $R_6$ are substituents, they can be any of those substituents described above as substituents on the benzo or phenoxy rings, or any of the other substituents described. As for $R_7$, $R_8$ and $R_9$, when any of these are an alkyl group they may, for example, have from 1 to 20 C atoms (or 1 to 10 or 1 to 6, such as methyl, ethyl, propyl, butyl or pentyl). Substituents include alkoxy (particularly 1 to 6 carbon atoms), halogen (particularly Cl and F), and cyano.

The compounds of formula (IA) may particularly be of formula (Ia) below:

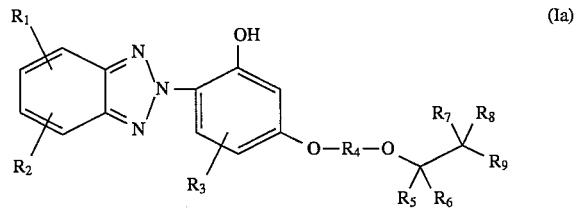

or more particularly of formula (Ib):

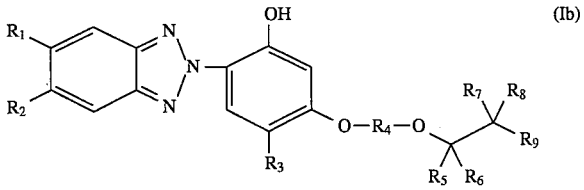

More particularly, in any of the above formula (Ia) or (Ib), $R_1$, $R_2$ and $R_3$ may be, independently, 1 to 18 (or 1 to 10, 1 to 6, or 1 to 2) carbon alkyl or alkoxy either of which may have 1–5 (or 1 or 2) intervening oxygen, sulfur or nitrogen atoms, or are aryl, heteroaryl, or aryloxy. $R_1$, $R_2$ and $R_3$ may also be, independently any of the foregoing substituted with 1 to 17 (or 1 to 10, 1 to 6, or 1 or 2) carbon alkoxy, 1 to 17 (or 1 to 10, 1 to 6, or 1 or 2) carbon alkyl sulfide, 0 to 17 carbon amino (or 0 to 10, 0 to 6, or 0 to 2), or a halogen, or any of $R_1$, $R_2$ or $R_3$ may be H or a halogen (particularly chloro or fluoro) or both $R_1$ and $R_2$ together form a 5 to 18 carbon atom aryl group (such as a benzo ring) or heteroaryl ring group (for example, pyrrolo, furyl, thienyl, pyridyl). Substituents on the foregoing rings formed by $R_1$ and $R_2$ may include a 1 to 17 (or 1 to 10, 1 to 6, or 1 or 2) carbon atom alkyl or alkoxy, or a halogen.

$R_1$, $R_2$ and $R_3$ may also be, independently: a chloro; a fluoro; a hydroxy; a cyano; a carboxy; a carbalkoxy; a nitro; an acylamino group (for example, an acetylamino group), carbamoyl, sulfonyl, sulfamoyl, sulfonamido, acyloxy (for example, an acetoxy group or a benzoyloxy group), or an oxycarbonyl group (for example, a methoxycarbonyl group, etc.), any of which may have 1 to 18 (or 1 to 10, 1 to 6, or 1 to 2) carbon atoms. $R_3$ is preferably be a 6'-position substituent, and most preferably a 6'-hydroxy.

Also, in any of the above formula, $R_4$ may particularly have a total of 2 to 20 (or 2 to 10, or 2 to 4) atoms and be an alkylene group which may have 1–5 (or 1, 2 or 3) intervening oxygen, sulfur or nitrogen atoms. Substituents on $R_4$ include, for example, a 1 to 10 (or 1 to 6, or 1 or 2)

carbon alkoxy, a 1 to 10 (or 1 to 6, or 1 or 2) carbon atom alkyl sulfide, 0 to 10 (or 0 to 6, or 0 to 2) carbon amino, or with halogen. $R_4$ may particularly be an unsubstituted propylene (that is, 3 carbon atoms in length with no intervening heteroatoms) or a propylene substituted with 1 to 12 (or 1, 2 or 3) carbon atom alkyl or alkoxy (either with or without 1 or 2 intervening oxygen atoms), or with a 0 to 6 (or 0, 1, 2, or 3) carbon atom amino, or a halogen (such as F or Cl).

UV absorbing compounds of formula (Ia) can be prepared from the chromophore of Formula (VI) below or by similar procedures. Other compounds of formula (I) can be prepared in a similar manner. The compounds of Formula (VI) can be easily synthesized from inexpensively available starting materials such as o-nitro-aniline, resorcinol, phloroglucinol, 4-chlororesorcinol etc. The synthesis of these compounds was accomplished by known procedures. These procedures are described in M. Karvas and J. Holcik., *Chemicky Prumysl*, 17 (1), 543 (1967); *Chemical Abstract* 70 (12): 48169j (1969), and U.S. Pat. No. 3,072,585. Formula (VI) has the structure:

pound (VII) has the structure:

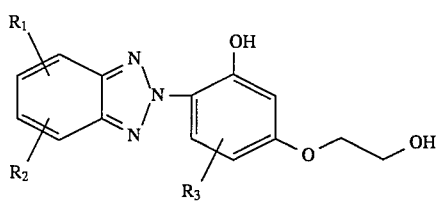

where, $R_1$, $R_2$ or $R_3$ have the same meanings as described for Formula (Ia) above.

The novel easily dispersible low melting solid UV absorbing compounds, represented by Formula (VIII), were easily prepared by the method shown in Scheme I below, by reacting with inexpensive racemic 2-ethylhexyl glycidyl ether in the presence of ethyl triphenylphosphonium bromide as a phase-transfer catalyst. This procedure is described by David G. Leppard and Kurt Burdeska in European Patent Application EP 521,823. Tetra alkyl ammonium chlorides or bromides may also be used as phase-transfer catalysts.

Scheme I

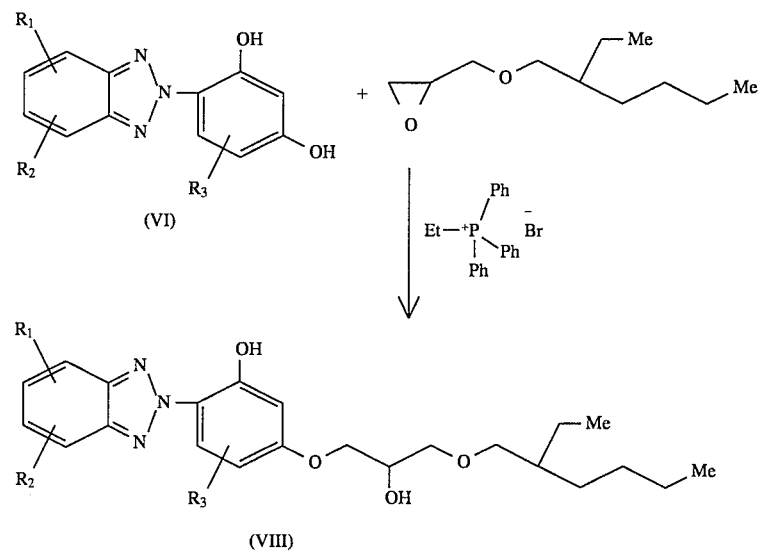

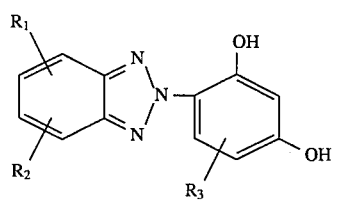

where, $R_1$, $R_2$ or $R_3$ have the same meanings as described for Formula (Ia).

The conversion of (VI) to 2H-[2'-hydroxy, 4'-(2-hydroxyethoxy)phenyl]benzotriazoles (VII) is in general preferably accomplished by the procedure described in U.S. patent application filed by Vishwakarma on Sep. 27, 1994 (Ser. No. 08/313,492), entitled "Benzotriazole Based UV Absorbing Monomers and Photographic Elements Containing Polymers Formed From Them" (Attorney Docket No. 68,906). That application, and all other references cited herein, are incorporated in the present application by reference. Com- Details of the preparation of compounds of the present invention of formula (VIII) are described in Examples 1–5 below. The yields and physical properties of the inventive compounds of Formula (VIII) are summarized in Table 1.

Similar compounds, but without an asymmetric carbon, were synthesized as comparative compounds to illustrate the advantages of the present invention. These comparative compounds are identified as compounds (IX), (X), (XI), and (XII). Details of their synthesis are provided below in Examples 6–9. As shown in Table 3 (see "Photographic Evaluation" section below), these comparative compounds crystallized out in the dispersion as well in the coatings under identical test conditions. This shows an advantage of the presently claimed compounds, with an asymmetric carbon versus similar compounds without such an asymmetric carbon, (that is, non-racemic carbon center).

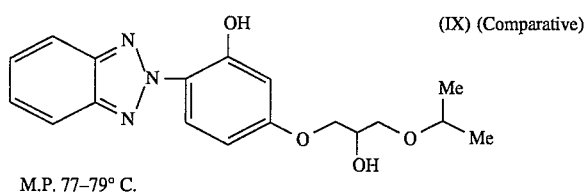

M.P. 77–79° C.  (IX) (Comparative)

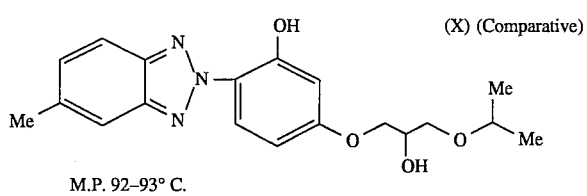

M.P. 92–93° C.  (X) (Comparative)

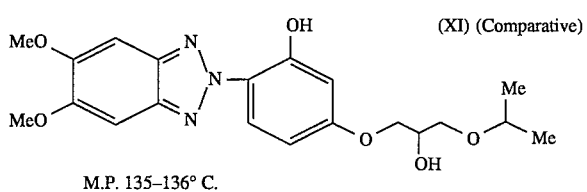

M.P. 135–136° C.  (XI) (Comparative)

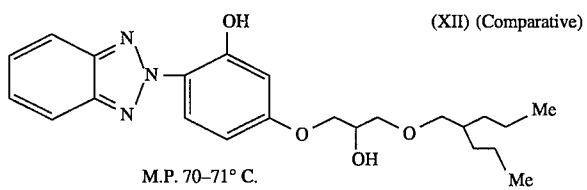

M.P. 70–71° C.  (XII) (Comparative)

UV absorbing compounds from Table 1 which are solid at room temperature (about 20° C.) can be desirably converted into liquid compounds by eliminating the hydrogen bonding effect of the secondary alcoholic group just by acetylating that group. Alternatively, in difficult cases they can be converted to liquid compounds (at room temperature) by adding at least one more racemic carbon center to the multiple ether linking chain. Other solid compounds of Table 1 were successfully converted to liquid.

The compounds VIII-A through VIII-E (Table 1) can be converted to compounds of the generic Formula (XIII) below. It is important that $R_{10}$, $R_{11}$ and $R_{12}$ are different such that the terminal carbon bearing those groups is asymmetric (a racemic carbon center) and have the same meaning as $R_7$, $R_8$ and $R_9$ in Formula (IA) above. The group $R_{13}$ is an acyl group which may or may not contain an alkyl group with racemic carbon center(s).

When $R_{13}$ also contains an asymetric carbon (or any other substituent also contains an asymmetric carbon), such that there are two or more asymmetric carbons in the compound, diastereomers can then be formed. This means that the UV absorbing compound of formula (I) could then have more than one pair of enantiomers. However, the compound should preferably have a 60/40 to 40/60 (preferably 50/50) ratio of at least two enantiomers (although it can have, for example a 60/40 to 40/60 ratio of enantiomers in each of two sets of enantiomers).

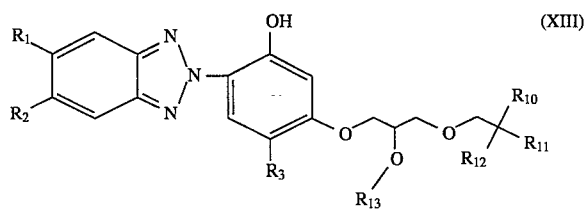

(XIII)

The hydrogen-bonding effect of the secondary alcoholic group (that is, when $R_{13}$=H) may be eliminated either by its etherification, reductive deoxygenation or acylation. A selective alkylation of the secondary alcohol group particularly in the presence of phenolic OH group would be difficult and expensive. Reductive deoxygenation of the secondary alcoholic group could be achieved following an analogous procedure known in the art. See, H. Sano, M. Ogata, and T. Migita, *Chemistry Letters*, (1), 77 (1986); and R. H. Wollenberg, and S. J. Miller, *Tetrahedron Letters*, 3219 (1978). However, acid-catalyzed esterification with a carboxylic acid appeared to be an economical synthetic step as known with the non-benzotriazole class of compounds. [See, D. K. Banerjee, et al, *Tetrahedron*, 20, 2487 (1964); W. S. Johnson, and E. R. Rogier, J. Ackerman, *Journal of American Chemical Society*, 78, 6289, 6306, 6322 (1956); C. G. Overberger, and P. V. Bonsignore, *Journal of American Chemical Society*, 80, 5427 (1958); and K. Mori, and M. Waku, *Tetrahedron*, 41 (23), 5653 (1985).

Specific compounds of the present invention of generic formula (XIII) are listed in Table 2 below. Those compounds were easily synthesized by acid-catalyzed esterification with a carboxylic acid. See, D. K. Banerjee, et al, *Tetrahedron*, 20, 2487 (1964). p-Toluenesulfonic acid monohydrate was used as a catalyst. Other compounds of formula (XIII) can be similarly prepared. Only 1.5–2.0 mole equivalent of higher boiling carboxylic acids were used while glacial acetic acid may be used in excess. The excess glacial acetic was easily removed on a rotary evaporator. Details of the synthesis of some of the Formula (XIII) compounds are provided below under Examples 10–17. Physical properties of Formula (XIII) compounds of the present invention, are listed below in Table 2.

The foregoing type of esterification also worked well with benzotriazole of structure (VII) containing primary alcoholic functional group.

The following two new UV compounds (XIV) and (XV) were made from Formula (VII) for photographic evaluation. Details of their synthesis are provided in Examples 18 and 19 below. These two compounds are structurally different from similar ones reported in EP 0 451 813. In the reported compounds, the intervening ester linkage has a different arrangement.

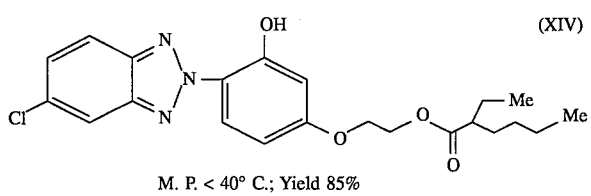

M. P. < 40° C.; Yield 85%

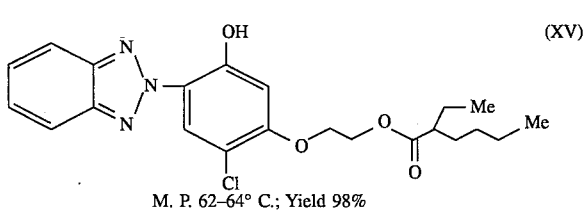

M. P. 62–64° C.; Yield 98%

Photographic elements according to the present invention will typically have at least one light sensitive silver halide emulsion layer and a non-light sensitive layer, with the ultraviolet absorbing compound of formula (I) being typically (but not necessarily) located in the non-light sensitive layer. More preferably, a photographic element of the present invention will have the non-light sensitive layer containing the ultraviolet absorbing compound located above all light sensitive layers. However, it is also contemplated that the ultraviolet absorbing compound can additionally be present in another layer, such as an interlayer (or even a light sensitive layer), particularly an interlayer located between red and green sensitive layers in an element having blue, green and red-sensitive layers coated in that order, on a support (particularly a paper support). Any layer of the photographic element in which the UV absorbing compounds of formula (I) are located will normally be a gel layer, and the UV absorbing compound may particularly be dispersed therein using a coupler solvent with or without additional ethyl acetate.

The UV absorbing compounds can be directly dispersed in the element or dispersed therein in droplets of a solvent dispersion. Alternatively, the UV absorbing compounds of formula (I) can be loaded into a polymer latex by themselves or with other compounds such as high boiling point organic solvents or monomeric UV absorbing compounds. "Loading" a polymer latex is generally described in U.S. Pat. No. 4,199,363 for example. Loading of a polymer latex is also described, for example, in U.S. Pat. Nos. 4,203,716, 4,214,047, 4,247,627, 4,497,929 and 4,608,424.

As described, UV absorbing compounds of the present invention are preferably used by themselves in a photographic element. However, they may be used in conjunction with other UV absorbing compounds if desired, such as other benzotriazole based UV absorbers. Examples of such conventional UV absorbing agents which can be used include: 2-(2-hydroxy-5-methylphenyl)-2H-benzotriazole, 2-(2-hydroxy-3,5-di-tert-butylphenyl)-2H-benzotriazole, 2-(2-hydroxy-3-tert-butyl-5-methylphenyl)-2H-benzotriazole, 2-(2-hydroxy-3,5-di-tert-butylphenyl)-5-chloro-2H-benzotriazole, 2-(2-hydroxy-3,5-di-tert-amylphenyl)-2H-benzotriazole, 2-(2-hydroxy-3,5-di(1,1-dimethylbenzyl)-phenyl)-2H-benzotriazole, 2-(2-hydroxy-5-tert-octylphenyl)-2H-benzotriazole. Other types of UV absorbing agents such as p-hydroxybenzoates, phenylesters of benzoic acid, salicylanilides and oxanilides, diketones, benzylidene malonate, esters of α-cyano-cinnamic acid, and organic metal photostabilizers, and others, as described in J. F. Rabek, *Photostabilization of Polymers, Principles and Applications*, Elsevier Science Publishers LTD, England, page 202–278(1990).

The UV absorbing compound is incorporated into the photographic element (typically into a gelatin gel thereof) in an amount of between 0.2 $g/m^2$ to 10 $g/m^2$, and more preferably between 0.5 $g/m^2$ to 5.0 $g/m^2$. Furthermore, when incorporated as a solvent dispersion using a water immiscible organic solvent, the weight ratio of high boiling, water immiscible organic solvent to UV absorbing compound is preferably between 0.1 to 5.0 (that is, 0.1/1 to 5.0/1 of solvent/UV absorbing compound), and more preferably between 0.2 to 3.0 (that is, 0.2/1 to 3.0/1 of solvent/UV absorbing compound).

The UV absorbing compound of formula (I) is provided in any one or more of the layers (for example, a hydrophilic colloid layer such as a gelatin layer) of a photographic light-sensitive material (for example, a silver halide photographic light-sensitive material), such as a surface protective layer, an intermediate layer or a silver halide emulsion layer, and the like. For example, in photographic paper the UV absorbing compound of formula (I) with/without other UV absorbing compounds, may be positioned above and/or below the red sensitive layer (typically adjacent to it), the red sensitive layer typically being the uppermost light sensitive layer in color paper, or even completely or partially within the red sensitive layer. The UV absorbing compound is typically provided in a given layer of a photographic element by coating the hydrophilic colloid material (such as a gelatin emulsion) which contains the latex, onto a support or another previously coated layer forming part of the element.

The photographic elements made by the method of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical.

The present invention also contemplates the use of photographic elements of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in elements of this invention, reference will be made to *Research Disclosure*, September 1994, Number 365, Item 36544, published by Kenneth Mason Publications, Ltd., Dudley Annex, 12a North Street, Emsworth, Hampshire P010 7DQ, ENGLAND, which will be identified hereafter by the term "Research Disclosure I." The Sections hereafter referred to are Sections of the Research Disclosure I.

The silver halide emulsions employed in the elements of this invention can be either negative-working, such as surface-sensitive emulsions or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through V. Color materials and development modifiers are described in Sections V through XX. Vehicles which can be used in the elements of the present invention are described in Section II, and various additives such as brighteners, antifoggants, stabilizers, light absorbing and scattering materials, hardeners, coating aids, plasticizers, lubricants and matting agents are described, for example, in Sections VI through X and XI through XIV. Manufacturing methods are described in all of the sections, other layers and supports in Sections XI and XIV, processing methods and agents in Sections XIX and XX, and exposure alternatives in Section XVI.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213 490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; U.S. Pat. Nos. 4,420,556; and 4,543,323.) Also, the couplers may be blocked or coated in protected form as described, for example, in Japanese Application 61/258,249 or U.S. Pat. No. 5,019,492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607, 004; 4,618,571; 4,678,739; 4,746,600; 4,746,601; 4,791, 049; 4,857,447; 4,865,959; 4,880,342; 4,886,736; 4,937, 179; 4,946,767; 4,948,716; 4,952,485; 4,956,269; 4,959, 299; 4,966,835; 4,985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. Nos. 4,346,165; 4,540,653 and 4,906, 559); with ballasted chelating agents such as those in U.S. Pat. No. 4,994,359 to reduce sensitivity to polyvalent cations such as calcium; and with stain reducing compounds such as described in U.S. Pat. Nos. 5,068,171 and 5,096,805. Other compounds useful in the elements of the invention are disclosed in Japanese Published Applications 83-09,959; 83-62,586; 90-072,629, 90-072,630; 90-072,632; 90-072, 633; 90-072,634; 90-077,822; 90-078,229; 90-078,230; 90-079,336; 90-079,338; 90-079,690; 90-079,691; 90-080, 487; 90-080,489; 90-080,490; 90-080,491; 90-080,492; 90-080,494; 90-085,928; 90-086,669; 90-086,670; 90-087, 361; 90-087,362; 90-087,363; 90-087,364; 90-088,096; 90-088,097; 90-093,662; 90-093,663; 90-093,664; 90-093, 665; 90-093,666; 90-093,668; 90-094,055; 90-094,056; 90-101,937; 90-103,409; 90-151,577.

The silver halide used in the photographic elements of the present invention may be silver iodobromide, silver bromide, silver chloride, silver chlorobromide, silver chloroiodobromide, and the like. The type of silver halide grains preferably include polymorphic, cubic, and octahedral. The grain size of the silver halide may have any distribution known to be useful in photographic compositions, and may be ether polydipersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where
ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: *Research Disclosure*, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains to be used in the invention may be prepared according to methods known in the art, such as those described in *Research Disclosure I* and James, *The Theory of the Photographic Process*. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions.

The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30° to 80° C., as illustrated in *Research Disclosure*, June 1975, item 13452 and U.S. Pat. No. 3,772,031.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in *Research Disclosure I*, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements comprising the composition of the invention can be processed in any of a number of well-known photographic processes utilizing any of a number of well-known processing compositions, described, for example, in *Research Disclosure I*, or in T. H. James, editor, *The Theory of the Photographic Process*, 4th Edition, Macmillan, New York, 1977. In the case of processing a reversal color element, the element is first treated with a black and white developer followed by treatment with a color developer. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(β-(methanesulfonamido) ethylaniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

Development is followed by bleach-fixing, to remove silver or silver halide, washing and drying.

The present invention will be further described in the examples below.

The following specific examples illustrate the various aspects of this invention but are not intended to limit its scope.

EXAMPLE 1

Inventive Compound No. VIII-A, Table 1

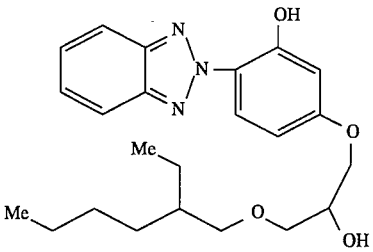

A mixture of 2H-(2,4-dihydroxyphenyl)benzotriazole (45.4 g, 0.2 mole), 2-ethylhexyl glycidyl ether (38.0 g, 0.2 mole, 98% pure from Aldrich) and tetramethyl ammonium chloride (0.8 g, 0.0073 mole, 4% equivalent) was heated in an oil bath at 70° C. while magnetically stirring for 24 hours. The reaction mixture became a dark-brown viscous liquid. The HPLC assay of an aliquot showed 25% unreacted starting benzotriazole. Purification of the crude liquid by silica gel flash column chromatography (elution solvent: heptane/acetone; 1000 mL/10 mL) afforded 53.7 g. (65% yield) of the pure product. In a separate experiment with ethyl triphenyl phosphonium bromide phase-transfer catalyst, cleaner and better yield was obtained]. Its retention time in HPLC was 20.22 min. Elemental analysis for $C_{23}H_{31}N_3O_4$ (M. W. 413.4): Calcd. C, 66.81; H, 7.56; N, 10.16. Found: C, 66.45; H, 7.37; N, 10.12; It had important IR bands at 3401 (s, alcoholic OH), 3095, 2954, 2930, 2872, 1713, 1619, 1602, 1502, 1255, 1190, 1120, 1067, 1044, 973 and 750 cm$^{-1}$. It had NMR peaks in (CDCl$_3$) at δ 11.40 (phenolic OH, s, 1H), 8.32 (d, 1H, arom.), 7.92 (m, 2H, arom), 7.45 (m, 2H, arom), 6.72 (d, 1H, arom.), 6.63 (m, 2H, arom.), 4.2 (m, 1H, methine), 4.10 (m, 2H, CH$_2$), 3.6 (m, 2H, CH$_2$), 3.38 (d, 2H, CH$_2$), 2.58 (d, 1H, alcoholic OH, exchangeable with D$_2$O), 1.53 (m, 1H, methine), 1.28 (two doublets merged with a tall singlet, 8H, 4×CH$_2$'s) and 0.9 (t, 6H, 2×CH$_3$'s).

EXAMPLE 2

Inventive Compound No. VIII-B, Table 1

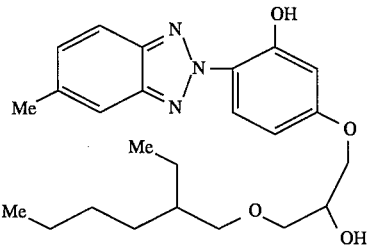

This dye was prepared using toluene as the reaction solvent. A mixture of 2H-(2,4-dihydroxyphenyl)-5-methylbenzotriazole (26.5 g, 0.11 mole), 2-ethylhexyl glycidyl ether (23.6 g, 0.13 mole, 15% excess, 98% pure from Aldrich) and tetramethyl ammonium chloride (0.55 g, 0.005 mole) in 100 mL of toluene was heated in an oil bath at 105° C. while magnetically stirring under argon. The reaction was slow (only 50% after 4 hours). Then 48 g more of 2-ethylhexyl glycidyl ether was added and heated at 90° C. for an additional 16 hours. The HPLC assay still remained the same. The product was distilled under high vacuum using Kugl Rohr Distillation Apparatus. B. P. was 240° C. at 0.15 mm Hg pressure. This solidified at room temperature and had M.P. <50° C. The total yield was only 4.3 g. The result was superior when reaction was carried out without a solvent particularly in the presence of ethyl triphenyl phosphonium bromide phase-transfer catalyst where product may be obtained in over 75% yield and no excess of 2-ethylhexyl glycidyl ether was required. Its retention time in HPLC was 21.12 min. Elemental analysis for $C_{24}H_{33}N_3O_4$ (M.W. 427.5): Calcd. C, 67.42; H, 7.78; N, 9.83. Found: C, 67.17; H, 7.76; N, 9.86. Important IR bands were at 3460, 2872, 1713, 1619 and 1596 cm$^{-1}$. It had NMR peaks in (CDCl$_3$) at δ 11.4 (phenolic OH, s, 1H), 8.21 (d, 1H, arom.), 7.68 (d, 1H, arom), 7.5 (s, 1H, arom.), 7.23 (d, 1H, arom), 6.7 (s, 1H, arom.), 6.6 (2 doublets, 1H, arom) 4.18 (m, 1H, methine), 4.1 (m, 2H, methylene), 3.58 (d, 2H, CH$_2$), 3.38 (d, 2H, CH$_2$), 2.58 (d, 1H, alcoholic OH, exchangeable with D$_2$O), 2.5 (s, 3H, CH$_3$), 1.5 (m, 1H, methine), 1.3 (m, 8H, 4×CH$_2$'s) and 0.9 (t, 6H, 2×CH$_3$'s).

EXAMPLE 3

Inventive Compound No. VIII-C, Table 1

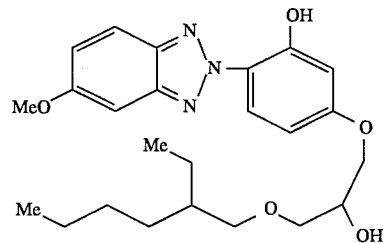

This dye was prepared using toluene as the reaction solvent. A mixture of 2H-(2,4-dihydroxyphenyl)-5-methoxybenzotriazole (25.7 g, 0.10 mole), 2-ethylhexyl glycidyl ether (20.9 g, 0.11 mole, 10% excess, 98% pure from Aldrich) and tetramethyl ammonium chloride (0.4 g, 0.00365 mole, 3.6% equivalent) in 100 mL of toluene was heated in an oil bath at 90°–100° C. while magnetically stirring for 12 hours when about 55% conversion (by HPLC of an aliquot) was achieved. Then 20 g more of 2-ethylhexyl glycidyl ether and 0.4 g more of the catalyst were added and heated at 90° C. for an additional 16 hours. The HPLC assay increased to 72%. The product was distilled under high vacuum using Kugl Rohr Distillation Apparatus. B. P. was 245°–250° C. at 0.15 mm Hg pressure. This solidified at room temperature and had M.P. 52°–53° C. The yield was 30.32 g (68%). The result was superior when reaction was carried out without a solvent particularly in the presence of ethyl triphenyl phosphonium bromide phase-transfer catalyst where product may be obtained in over 75% yield and no excess of 2-ethylhexyl glycidyl ether would be required. Its retention time in HPLC was 20.26 min. Its TLC (Heptane/Acetone; 7.5/2.5) shoed an Rf 0.39. Elemental analysis for $C_{24}H_{33}N_3O_5$ (M.W. 443.5): Calcd. C, 64.99; H, 7.50; N, 9.47. Found: C, 64.89; H, 7.62; N, 9.07; It had NMR peaks in (CDCl$_3$) at δ 11.8 (phenolic OH, s, 1H), 8.2 (d, 1H, arom.), 7.7 (d, 1H, arom), 7.1 (m, 2H, arom.), 6.68 (d, 1H, arom), 6.6 (2 doublets, 1H, arom.), 4.18 (quintet, 1H, methine), 4.08 (m, 2H, methylene), 3.9 (s, 3H, OMe), 3.6 (m, 2H, CH$_2$), 3.58 (d, 2H, CH$_2$), 2.58 (d, 1H, alcoholic OH, exchangeable with D$_2$O), 1.5 (m, 1H, methine), 1.25 (m, 8H, 4×CH$_2$'s ) and 0.85 (t, 6H, 2×CH$_3$'s).

EXAMPLE 4

Inventive Compound No. VIII-D, Table 1

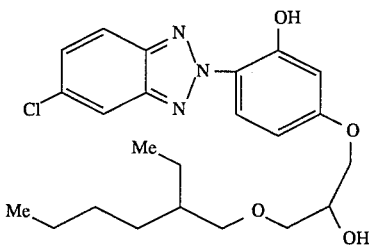

A mixture of 2H-(2,4-dihydroxyphenyl)-5-chlorobenzotriazole (8.64 g, 0.033 mole), 2-ethylhexyl glycidyl ether (10.69 g, 0.057 mole, 98% pure from Aldrich) and tetramethyl ammonium chloride (0.2 g, 0.0018 mole, 5.5% equivalent) was mechanically stirred in an oil bath raising the temperature gradually from 90° C. to 145° C. at a rate of 2° C./min. When the reaction mixture became a brown liquid, the temperature was held at 145° C. for 3 hours TLC indicated the reaction was nearly complete. Purification of the crude liquid by silica gel flash column chromatography (elution solvent: ligroin/ethyl acetate; 85/15 ratio or $CH_2Cl_2$/MeOH; 9.5/0.5 ratio) afforded 5.6 g. (37.8% yield) of the pure product. A separate experiment with ethyl triphenyl phosphonium bromide phase-transfer catalyst gave 70% yield of the product. Its retention time in HPLC was 21.26 min. It TLC ($CH_2Cl_2$/MeOH; 9.5/0.5) showed an Rf 0.57. Elemental analysis for $C_{23}H_{30}Cl_1N_3O_4$ (M.W. 448): Calcd. C, 61.67; H, 6.75; N, 9.38. Found: C, 61.66; H, 6.74; N, 9.48. It had important IR bands at 3425 (s, alcoholic OH), 3096, 2955, 2919, 2872, 1713, 1625, 1595, 1455, 1384, 1261, 1126, 1050, 979, 820, 808, 714 and 597 $cm^{-1}$. It had NMR peaks in ($CDCl_3$) at $\delta$ 11.15 (phenolic OH, s, 1H), 8.22 (d, 1H, arom.), 7.88 (m, 1H, arom), 7.81 (d, 1H, arom), 7.38 (d, 1H, arom), 6.65 (s, 1H, arom.), 6.61 (d, 1H, arom.), 4.18 (broad singlet, 1H, methine), 4.02 (d, 2H, $CH_2$), 3.58 (m, 2H, $CH_2$), 3.35 (d, 2H, $CH_2$), 2.52 (broad singlet, 1H, alcoholic OH, exchangeable with $D_2O$), 1.5 (m, 1H, methine), 1.22 (m, 8H, 4×$CH_2$'s) and 0.88 (t, 6H, 2×$CH_3$'s).

EXAMPLE 5

Inventive Compound No. VIII-E, Table 1

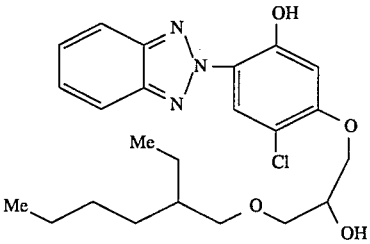

A mixture of 2H-(2,4-dihydroxy-5-chlorophenyl)benzotriazole (30.1 g, 0.115 mole), 2-ethylhexyl glycidyl ether (24.64 g, 0.132 mole, 15% excess, 27.7 mL, 98% pure from Aldrich) and ethyl triphenyl phosphonium bromide (4.26 g, 0.0115 mole, 10% equivalent) was mechanically stirred in an oil bath raising the temperature gradually to 120° C. at a rate of 2° C./min. When the reaction mixture became a brown liquid, the temperature was held at 145° C. for 3–4 hours until the reaction mixture solidified. The temperature was brought down to 80° C. and acetone (150 mL) was added cautiously. This was cooled to room temperature and poured into 1.5L of iced-water containing sodium chloride. The precipitate was filtered, washed with cold water, air-dried and purified by flash column chromatography eluting with $CH_2Cl_2$/MeOH (995 mL/5 mL). [The crude material also could be recrystallized from an aqueous methanol]. The solvent from the eluent was removed. The solid residue was triturated with pentane, filtered, washed again with pentane and air-dried. The product was obtained as a white solid (37.6 g) in 73% yield. The yield was not optimized. Its retention time in HPLC was 21.14 min. Its TLC ($CH_2Cl_2$/MeOH; 9.5/0.5) showed an Rf 0.6. Elemental analysis for $C_{23}H_{30}Cl_1N_3O_4$ (M.W. 448): Calcd. C, 61.67; H, 6.75; N, 9.38; Cl, 7.91. Found: C, 61.49; H, 6.76; N, 9.31; Cl, 7.77. It had NMR peaks in ($CDCl_3$) at $\delta$ 11.5 (phenolic OH, s, 1H), 8.4 (s, 1H, arom.), 7.88 (m, 2H, arom), 7.42 (m, 2H, arom), 6.7 (s, 1H, arom.), 4.20 (m, 1H, methine), 4.10 (d, 2H, $CH_2$), 3.7 (two doublets, 1H, OH), 3.6 (d, 2H, $CH_2$), 3.38 (d, 2H, $CH_2$), 1.5 (m, 1H, methine), 1.4 - 1.1 (m, 8H, 4×$CH_2$'s) and 0.8 (t, 6H, 2×$CH_3$'s).

EXAMPLE 6

Comparative Compound No. IX

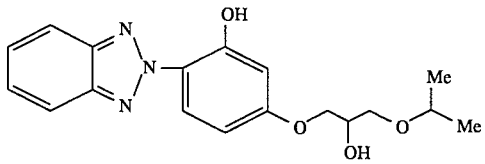

A mixture of 2H-(2,4-dihydroxyphenyl)benzotriazole (22.7 g, 0.1 mole), glycidyl isopropyl ether (13.94 g, 0.12 mole) and tetramethyl ammonium chloride (0.55 g, 0.005 mole) was heated in an oil bath gradually raising the temperature to 80° C. while magnetically stirring for 16 hours. A dark brown viscous material (35 g) was obtained. Its HPLC analysis showed 18% (peak area) of starting triazole, 61% (peak area) of desired product and 12% (peak area) of dialkylated product. Its purification by flash column chromatography (eluting with heptane/acetone; 99/1) gave 13 g (36% yield) of compound IX in a 97% purity. M.P. 77°–79° C. [Note: This reaction gives better results when carried out in the presence of ethyl triphenyl phosphonium bromide phase-transfer catalyst]. Its retention time in HPLC was 14.52 min. Its TLC (heptane/acetone; 9/1) showed an Rf 0.7. Elemental analysis for $C_{18}H_{21}N_3O_4$ (M.W. 343.4): Calcd. C, 62.96; H, 6.16; N, 12.24. Found: C, 62.99; H, 6.24; N, 12.10; It had important IR bands at 3425, 3237, 3095, 2966, 2931, 2872, 1713, 1631, 1596, 1514, 1290, 1178, 1120, 1067, and 738 $cm^{-1}$. It had NMR peaks in ($CDCl_3$) at $\delta$ 11.40 (s, 1H, phenolic OH), 8.28 (d, 1H, arom.), 7.9 (m, 2H, arom), 7.43 (m, 2H, arom), 6.71 (s, 1H, arom.), 6.65 (2 doublets, 1H, arom.), 4.15 (broad singlet, 1H, methine), 4.08 (distorted doublet, 2H, $CH_2$), 3.62 (m, 3H, 1 methine and 1 methylene in the isopropyl chain), 2.65 (broad singlet, 1H, alcoholic OH, exchangeable with $D_2O$), and 1.20 (d, 6H, 2×$CH_3$'s in the isopropyl group). Its UV-VIS (MeOH) showed a $\lambda_{max}$ 338 nm and an $\epsilon_{max}$ 2.33×$10^4$.

EXAMPLE 7

Comparative Compound No. X

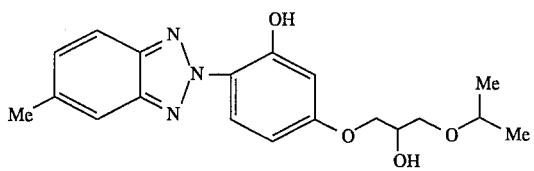

A mixture of 2H-(2,4-dihydroxyphenyl)-5-methylbenzotriazole (12.07 g, 0.05 mole), glycidyl ether isopropyl (7.6 g, 8.2 mL, 0.065 mole) and tetramethyl ammonium chloride (1.65 g, 0.015 mole, 30% equivalent) was heated in an oil bath gradually raising the temperature to 140° C. while mechanically stirring for 16 hours. As the temperature of the oil bath rose from 90° C. to 140° C., the reaction mixture became a brown colored melt. It was dissolved in $CH_2Cl_2$ (150 mL), coated on silica gel (100 g). Its purification by flash column chromatography (eluting with methylene chloride/methanol; 975 mL/25 mL) gave 1.56 g of desired product as a first fraction from the column. [Note: Most of the product was lost during purification in the fore-run. A combination of heptane/acetone should have been chosen for elution to avoid the mishap]. M.P. 92°–93° C. [Note: This reaction gives better results when carried out in the presence of ethyl triphenyl phosphonium bromide phase-transfer catalyst]. Its retention time in HPLC was 15.62 min. showing 100% purity by peak area. Its TLC (hexane/ethyl acetate; 5/5) showed an Rf 0.4. Elemental analysis for $C_{19}H_{23}N_3O_4$ (M.W. 357.4): Calcd. C, 63.85; H, 6.49; N, 11.76. Found: C, 63.81; H, 6.59; N, 11.84. It had NMR peaks in (CDCl$_3$) at δ 11.8 (s, 1H, phenolic OH), 8.23 (d, 1H, arom.), 7.78 (d, 1H, arom), 7.62 (s, 1H, arom), 7.24 (d, 1H, arom.), 6.7 (s, 1H, arom.), 6.62 (2 doublets, 1H, arom), 4.15 (m, 1H, methine), 4.10 (m, 2H, CH$_2$), 3.60 (m, 3H, 1 methine and 1 methylene), 2.5 (broad singlet, 4H, alcoholic proton peak merged with the methyl peak), and 1.20 (d, 6H, 2×CH$_3$'s in the isopropyl group). Its UV-VIS (MeOH) showed a $\lambda_{max}$ 340 nm and an $\epsilon_{max}$ 2.49×10$^4$.

EXAMPLE 8

Comparative Compound No. XI

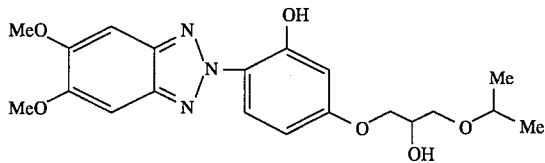

A mixture of 2H-(2,4-dihydroxyphenyl)-5, 6-dimethoxybenzotriazole (3.8 g, 0.0132 mole), glycidyl isopropyl ether (2.0 g, 2.2 mL, 0.0172 mole) and tetramethyl ammonium chloride (0.45 g, 0.004 mole, 30% equivalent) was heated in an oil bath gradually raising the temperature to 130° C. while mechanically stirring for 16 hours. As the temperature of the oil bath rose from 90° C. to 130° C., the reaction mixture became a brown colored melt. It was dissolved in $CH_2Cl_2$ (150 mL), coated on silica gel (100 g). Its purification by flash column chromatography (eluting methylene chloride/methanol; 975 mL/25 mL) gave 0.74 g of desired product as a first fraction from the column. [Note: In this case too, most of the product was lost during purification in the fore-run. A combination of heptane/acetone should have been chosen for elution to avoid the mishap]. M.P. 135°–136° C. A separate experiment with ethyl triphenyl phosphonium bromide as a phase-transfer catalyst gave about 70% yield of the desired product]. Its retention time in HPLC was 12.99 min. showing 98% purity (by peak area). Its TLC (hexane/ethyl acetate; 5/5) showed an Rf 0.24. Elemental analysis for $C_{20}H_{25}N_3O_6$ (M.W. 403.4): Calcd. C, 59.54; H, 6.25; N, 10.42. Found: C, 59.24; H, 6.24; N, 9.94. It had NMR peaks in (CDCl$_3$) at δ 11.6 (s, 1H, phenolic OH), 7.1 (s, 2H, arom.), 6.7 (s, 1H, arom.), 6.6 (2 doublets, 1H, arom), 4.17 (m, 1H, methine), 4.02 (d, 2H, CH$_2$), 4.0 (s, 6H, 2×OMe's), 3.6 (m, 3H, 1 methine and 1 methylene), 2.58 (d, 1H, alc. OH), and 1.20 (d, 6H, 2×CH$_3$'s in the isopropyl group). Its UV-VIS (MeOH) showed a $\lambda_{max}$ 345 nm and an $\epsilon_{max}$ 2.89×10$^4$.

EXAMPLE 9

Comparative Compound No. XII

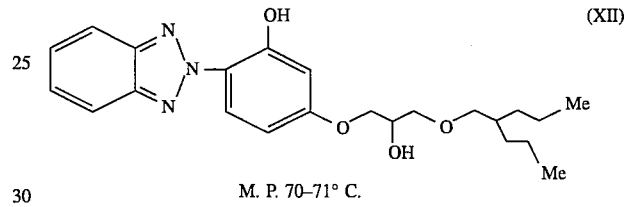

M. P. 70–71° C.

2-Propylpentyl gyycidyl ether was prepared following a procedure from the known art (See *Chemical Abstract*, 119 (7): 72481f; H. Morita, T. Inagi and T. Goto, *Japanese Kokai Tokkyo Koho* JP 05032650 A2 930209). This ether was used as a reactant in the synthesis of the Comparative Compound No. XII. This ether intermediate was used without further purification. Thus, a mixture of 2H-(2,4-dihydroxyphenyl-)benzotriazole (11.3 g, 0.05 mole), 2-propylpentyl glycidyl ether (crude, 11.35 g, 0.06 mole, 20% excess) and ethyl triphenyl phosphonium bromide (1.86 g, 0.005 mole, 10% equivalent) was heated in an oil bath at 110°–120° C. while mechanically stirring for 16 hours. The reaction mixture became a dark-brown viscous liquid after 1 hour as the temperature had reached 110° C. Purification of the crude liquid by silica gel flash column chromatography (elution solvent: heptane/acetone; 1000 mL/10 mL) afforded 7.76 g. (37.5% yield) of the pure product. Lower yield of this compound was due to impure 2-propylpentyl glycidyl ether, otherwise the reaction was quite clean and no other side product was seen on TLC. Its retention time in HPLC was 27.4 min. Elemental analysis for $C_{23}H_{31}N_3O_4$ (M.W. 413.4): Calcd. C, 66.81; H, 7.56; N, 10.16. Found: C, 66.65; H, 7.59; N, 10.25. It had NMR peaks in (CDCl$_3$) at δ 11.40 (phenolic OH, s, 1H), 8.28 (d, 1H, arom.), 7.9 (2 doublets, 2H, arom), 7.45 (2 doublets, 2H, arom), 6.7 (d, 1H, arom.), 6.3 (2 doublets, 1H, arom.), 4.18 (m, 1H, methine), 4.08 (d, 2H, CH$_2$), 3.6 (d, 2H, CH$_2$), 3.38 (d, 2H, CH$_2$), 2.5 (broad hump, 1H, alcoholic OH, exchangeable with D$_2$O), 1.6 (m, 1H, methine), 1.25 (tall multiplet, 8H, 4×CH$_2$'s) and 0.85 (t, 6H, 2×CH$_3$'s). Its UV-VIS (MeOH) showed a $\lambda_{max}$ 339 nm and an $\epsilon_{max}$ 2.39×10$^4$. Its melting point was 70°–71° C. Table 5 further illustrates improved intrinsic light stability of Inventive Compounds (XIII, Table 2), (XIV) and (XV) containing multiple ether/ester linkages over the Comparative Compounds (V-A) and (V-B). Even the 2 week HID and HIS stability data of the inventive compounds in this Table are far superior to those of the comparative compound III cited in the closest prior art.

General Esterification Procedure for Compounds of Table -1 Containing Secondary Alcoholic Group or for Compounds Having Primary Alcoholic Group The compounds containing a secondary or primary alcoholic group were reacted with 1.5–3.0 mole equivalent of high boiling racemic/or simple carboxylic acids in the presence of a catalytic amount (10–20% equivalent) of p-toluenesulfonic acid monohydrate for 2 to 24 hours at 100°–130° C. under mechanical stirring. Acetylation was an exception where glacial acetic acid (lower boiling carboxylic acid) was used as a refluxing solvent and a reactant. Acetic acid was easily removed or recovered on a rotary evaporator. In general cases, the excess carboxylic acid and the acid catalyst were neutralized with calculated or slightly excess amount of solid sodium bicarbonate in the reaction flask at room temperature. The crude product was then dissolved in dichloromethane (200 mL). Other low boiling hydrocarbon solvents such as hexane or heptane may also be used. Insoluble inorganic material was filtered through celite. Silica gel (100 g) was added to the filtrate. Solvent was removed on a rotary evaporator keeping the water bath temperature below 70° C. The purification on the crude silica gel coat was done by flash column chromatography eluting with dichloromethane. In some cases the purity of the crude product was over 95% after extracting with ethyl acetate and washing with water. In one case it was demonstrated (which may be generally applicable to all) that products in Table 2 could be obtained from compounds in Table 1 in situ in the same reaction flask. It may not even be necessary to purify the compounds in Table 1 for the next step. The products in Table 2 were obtained as a colorless low melting solid or a liquid.

EXAMPLE 10

Inventive Compound No. XIII-A, Table 2

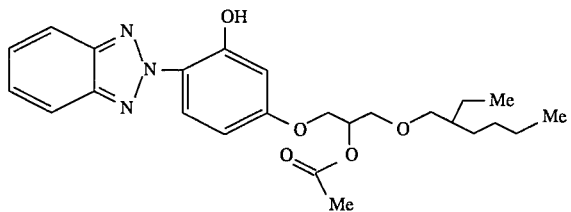

This is a liquid compound. It had NMR peaks in (CDCl$_3$) at δ 11.60 (phenolic OH, s, 1H), 8.28 (d, 1H, arom.), 7.9 (m, 2H, arom), 7.48 (m, 2H, arom), 6.7 (d, 1H, arom.), 6.62 (2 doublets, 1H, arom.), 5.3 (m, 1H, methine adjacent to acetate), 4.2 (merged quartets, 2H, methine), 3.68 (d, 2H, CH$_2$), 3.38 (merged quartets, 2H, CH$_2$), 2.1 (s, 3H, COCH$_3$), 1.5 (m, 1H, methine), 1.26 (m, 8H, 4×CH$_2$'s) and 0.9 (two merged triplets, 6H, 2×CH$_3$'s). FD-MS: m/e 455 (M$^+$).

EXAMPLE 11

Inventive Compound No. XIII-B, Table 2

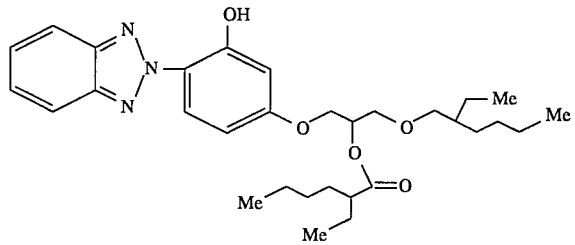

This is a liquid compound. It was purified by flash column chromatography eluting with dichloromethane. Its retention time in HPLC was 24.95 min. showing 92% purity of the crude material. Unreacted starting triazole (8–10%) was the only impurity in the crude product. This compound was made only to demonstrate the generality of the reaction. FD-MS: m/e 539 (M$^+$).

EXAMPLE 12

Inventive Compound No. XIII-C, Table 2

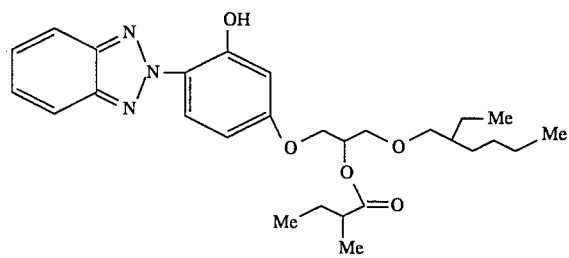

This is a liquid compound. It was purified by flash column chromatography eluting with dichloromethane. Its retention time in HPLC was 22.86 min. showing 90% purity of the crude material. Unreacted starting triazole (8–10%) was the only impurity in the crude product. For complete conversion, the reaction should be done at 150° C. This compound was made only to demonstrate the generality of the reaction. FD-MS: m/e 497 (M$^+$).

EXAMPLE 13

Inventive Compound No. XIII-E, Table 2

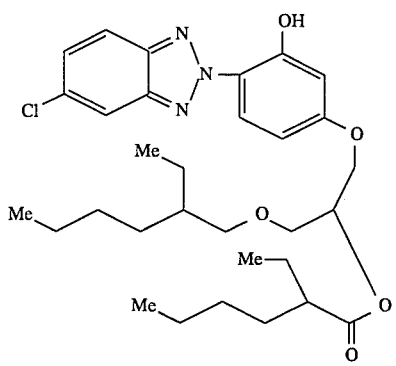

This is a liquid compound. Its retention time in HPLC was 26.8 min. Its TLC ($CH_2Cl_2$) showed Rf 0.6. FD-MS: m/e 573 (M$^+$). It had NMR peaks in ($CDCl_3$) at δ 11.20 (s, 1H, phenolic OH), 8.21 (d, 1H, arom.), 7.86 (d, 1H, arom), 7.6 (d, 1H, arom), 7.4 (d, 1H, arom), 6.64 (s, 1H, arom.), 5.4 (m, 1H, methine), 4.2 (distorted triplet, 2H, $CH_2$), 3.62 (distorted triplet, 2H, $CH_2$), 3.35 (distorted doublet, 2H, $CH_2$), 2.3 (m, 1H, methine), 1.58 (m, 6H, 3×$CH_2$'s), 1.3 (distorted singlet, 10H, 5×$CH_2$'s) and 0.82 (distorted triplets, 12H, 4×$CH_3$'s). Its UV-VIS (MeOH) showed a $\lambda_{max}$ 345 nm with an $\epsilon_{max}$ 2.22×10$^4$. Elemental analysis for $C_{31}H_{44}Cl_1N_3O_5$ (M.W. 574.2): Calcd. C, 64.85; H, 7.72; N, 7.32; Cl, 6.17. Found: C, 63.69; H, 7.96; N, 6.32; Cl, 5.66

EXAMPLE 14

Inventive Compound No. XIII-F, Table 2

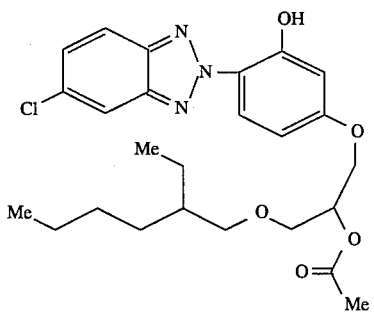

This is a solid compound having a melting point 42°–45° C. Its retention time in HPLC was 21.97 min. showing 99.4% purity (by peak area). It had NMR peaks in ($CDCl_3$) at δ 11.30 (s, phenolic OH, 1H), 8.22 (d, 1H, arom.), 7.9 (s, 1H, arom), 7.83 (d, 1H, arom), 7.4 (2 doublets, 1H, arom), 6.7 (s, 1H, arom.), 6.62 (2 doublets, 1H, arom.), 5.33 (m, 1H, methine adjacent to acetate), 4.2 (distorted triplet, 2H, $CH_2$), 3.68 (d, 2H, $CH_2$), 3.35 (distorted triplet, 2H, $CH_2$), 2.1 (s, 3H, $COCH_3$), 1.5 (m, 1H, methine), 1.23 (distorted singlet, 8H, 4×$CH_2$'s) and 0.84 (t, 6H, 2×$CH_3$'s). Its UV-VIS (MeOH) showed a $\lambda_{max}$ 345 nm with an $\epsilon_{max}$ 2.44×10$^4$. Elemental analysis for $C_{25}H_{32}Cl_1N_3O_5$ (M.W. 490): Calcd. C, 61.28; H, 6.58; N, 8.58. Found: C, 60.91; H, 6.55; N, 8.51.

EXAMPLE 15

Inventive Compound No. XIII-G, Table 2

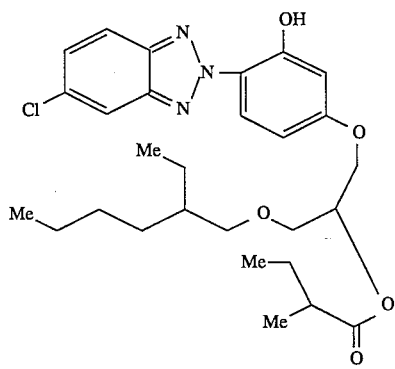

This is a liquid compound. Its retention time in HPLC was 23.78 min. showing 99.5% purity (peak area). It had NMR peaks in ($CDCl_3$) at δ 11.20 (s, 1H, phenolic OH), 8.22 (d, 1H, arom.), 7.9 (s, 1H, arom), 7.82 (d, 1H, arom), 7.4 (2 doublets, 1H, arom), 6.64 (s, 1H, arom.), 6.6 (d, 1H, arom), 5.35 (m, 1H, methine), 4.18 (distorted triplet, 2H, $CH_2$), 3.6 (d, 2H, $CH_2$), 3.3 (d, 2H, $CH_2$), 2.4 (m, 1H, methine), 1.5 (m, 2H, $CH_2$), 1.26 (distorted singlet, 8H, 4×$CH_2$'s), 1.18 (distorted doublet, 3H, $CH_3$) and 0.83 (distorted triplet, 9H, 3×$CH_3$'s). Its UV-VIS (MeOH) showed a $\lambda_{max}$ 345 nm with an $\epsilon_{max}$ 2.36×10$^4$. Elemental analysis for $C_{28}H_{38}Cl_1N_3O_5$ (M.W. 532.1): Calcd. C, 63.21; H, 7.20; N, 7.90. Found: C, 64.75; H, 7.75; N, 7.10.

EXAMPLE 16

Inventive Compound No. XIII-H, Table 2

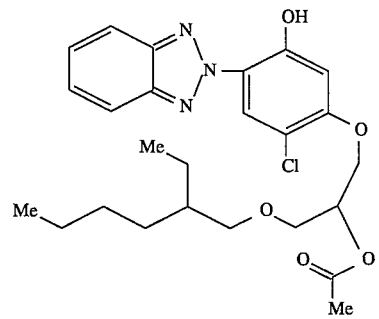

This is a liquid compound. Its retention time in HPLC was 22.11 min. showing 99% purity (peak area). Its TLC ($CH_2Cl_2$) showed Rf 0.39. It had NMR peaks in ($CDCl_3$) at δ 11.50 (s, 1H, phenolic OH), 8.4 (s, 1H, arom.), 7.9 (m, 2H, arom), 7.42 (m, 2H, arom), 6.7 (s, 1H, arom.), 5.32 (m, 1H, methine), 4.2 (m, 2H, $CH_2$), 3.7 (d, 2H, $CH_2$), 3.38 (m, 2H, $CH_2$), 2.1 (s, 3H, $OCOCH_3$), 1.5 (m, 1H, methine), 1.4 - 1.1 (m, 8H, 4×$CH_2$'s), and 0.88 (t, 6H, 2×$CH_3$'s). Its UV-VIS (MeOH) showed a $\lambda_{max}$ 343 nm with an $\epsilon_{max}$ 2.25×10$^4$. Elemental analysis for $C_{25}H_{32}Cl_1N_3O_5$ (M.W. 490): Calcd. C, 61.28; H, 6.58; N, 8.58; Cl, 7.24. Found: C, 61.38; H, 6.62; N, 8.51; Cl, 7.27.

EXAMPLE 17

Inventive Compound No. XIII-I, Table 2

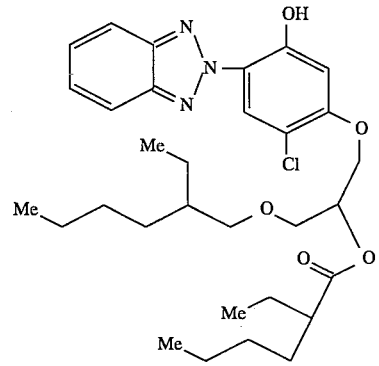

This is a liquid compound. Its retention time in HPLC was 27.13 min. showing 99% purity (peak area). Its TLC ($CH_2Cl_2$) showed Rf 0.54. It had NMR peaks in ($CDCl_3$) at δ 11.50 (s, 1H, phenolic OH), 8.4 (s, 1H, arom.), 7.9 (m, 2H, arom), 7.45 (m, 2H, arom), 6.7 (s, 1H, arom.), 5.4 (m, 1H, methine), 4.25 (m, 2H, CH$_2$), 3.7 (m, 2H, CH$_2$), 3.4 (d, 2H, CH$_2$), 2.32 (m, 1H, methine), 1.63 (m, 1H, methine), 1.48 (m, 4H, 2×CH$_2$'s), 1.28 (broad & tall singlet, 12H, 6×CH$_2$'s) and 0.88 (m, 12H, 4×CH$_3$'s). Its UV-VIS (MeOH) showed a $\lambda_{max}$ 343 nm with an $\epsilon_{max}$ 2.25×10$^4$. Elemental analysis for C$_{31}$H$_{44}$Cl$_1$N$_3$O$_5$ (M.W. 574.2): Calcd. C, 64.85; H, 7.72; N, 7.32. Found: C, 65.00; H, 7.70; N, 7.25.

EXAMPLE 18

Inventive Compound No. XIV

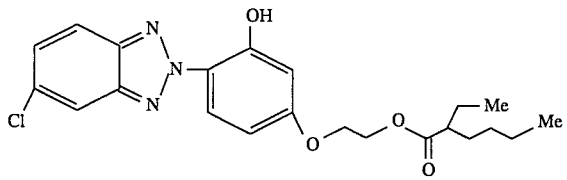

This compound was made in an 85% isolated yield following the previously described general procedure for esterification. M.P.<40° C. FD-MS: m/e 431 (M$^+$). Its retention time in HPLC was 21.3 min. showing 100% purity (by peak area). Its TLC (CH$_2$Cl$_2$) showed an Rf 0.48. It had NMR peaks in (CDCl$_3$) at δ 11.15 (s, 1H, phenolic OH), 8.2 (s, 1H, arom.), 7.83 (s, 1H, arom), 7.8 (d, 1H, arom), 7.38 (d, 1H, arom.), 6.62 (d, 1H, arom.), 6.6 (2 doublets, 1H, arom), 4.45 (t, 2H, CH$_2$), 4.2 (t, 2H, CH$_2$), 2.3 (m, 1H, methine), 1.7 - 1.4 (m, 4H, 2×CH$_2$'s), 1.28 (merged quartet, 4H, 2×CH$_2$CH$_3$'s) and 0.8 (t, 6H, 2×CH$_3$'s). Its UV-VIS (MeOH) showed a $\lambda_{max}$ 345 nm with an $\epsilon_{max}$ 2.44×10$^4$. Elemental analysis for C$_{22}$H$_{26}$Cl$_1$N$_3$O$_4$ (M.W. 431.9): Calcd. C, 61.18; H, 6.07; N, 9.73. Found: C, 61.43; H, 6.15; N, 9.56.

EXAMPLE 19

Inventive Compound No. XV

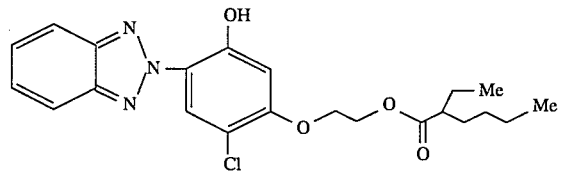

This compound was made in 98% yield following the previously described general procedure for esterification. M.P. 62°–64° C. FD-MS: m/e 431 (M$^+$). Its retention time in HPLC was 21.28 min. showing 100% purity (by peak area). Its TLC (CH$_2$Cl$_2$) showed an Rf 0.46. It had NMR peaks in (CDCl$_3$) at δ 11.5 (s, 1H, phenolic OH), 8.4 (s, 1H, arom.), 7.43 (m, 2H, arom), 6.7 (s, 1H, arom.), 4.5 (t, 2H, CH$_2$), 4.22 (t, 2H, CH$_2$), 2.3 (m, 1H, methine), 1.7 - 1.39 (m, 4H, 2×CH$_2$'s), 1.22 (distorted quartet, 4H, 2×CH$_2$CH$_3$'s) and 0.8 (2 triplets, 6H, 2×CH$_3$'s). Its UV-VIS (MeOH) showed a $\lambda_{max}$ 343 nm with an $\epsilon_{max}$ 2.19×10$^4$. Elemental analysis for C$_{22}$H$_{26}$Cl$_1$N$_3$O$_4$ (M.W. 431.9): Calcd. C, 61.18; H, 6.07; N, 9.73; Cl, 8.21. Found: C, 61.36; H, 6.15; N, 9.57; Cl, 8.28.

EXAMPLE 20

Inventive Compound No. XVI

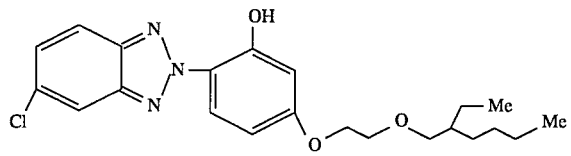

2H-(2-'hydroxy-4'-hydroxyethoxyphenyl)-5-chlorobenzotriazole (4.87 g, 0.0159 mole) was treated with potassium tert-butoxide (9.0 g, 0.08 mole, 5 mole equivalent) in dry dimethylsulfoxide (80 mL) for 15–20 min under argon with magnetic stirring. 4-Dimethylaminopyridine (0.58 g, 0.0048 mole) and tetramethylammonium chloride (0.53 g, 0.0048 mole) were added. 2-Ethylhexyl bromide (15.5 g, 14 mL, 0.08 mole, 5 mole equivalent) was added to the reaction mixture all at once. (Slight exotherm was obtained). The reaction mixture was stirred for 16 hours at room temperature. It was poured into 500 mL of ice-cold water containing 250 mL of brine. It was neutralized with glacial acetic acid to bring the pH to neutral (about 6–7). The product was extracted with ethyl acetate (3×200 mL), washed with cold water (4×200 mL), dried over anhydrous Na$_2$SO$_4$, filtered and solvent was removed on a rotary evaporator. Almost colorless viscous material was obtained. An HPLC assay of this material indicated a mixture of starting triazole (48% peak area), the desired product XVI (41% peak area) and dialkylated product (10% peak area). The product was isolated by flash column chromatography by eluting with ligroin (950). The residual material was recrystallized from isopropanol. A colorless solid (302 mg) was obtained. (Such a poor yield was due a to very difficult alkylation step which could be improved by heating the reation mixture). M.P. 50°–51° C. It had NMR peaks in (CDCl$_3$) at δ 11.20 (s, 1H, phenolic OH), 8.22 (d, 1H, arom.), 7.9 (d, 1H, arom), 7.82 (d, 1H, arom), 7.4 (2 doublets, 1H, arom), 6.7 (d, 1H, arom.), 6.63 (2 doublets, 1H, arom), 4.16 (t, 2H, CH$_2$), 3.8 (t, 2H, CH$_2$), 3.4 (d, 2H, CH$_2$ next to CH), 1.58 (m, 1H, methine), 1.3 (s, merged with multiplets, 8H, 4×CH$_2$'s), and 0.84 (t, 6H, 2×CH$_3$). Its UV-VIS (MeOH) showed a $\lambda_{max}$ 346 nm with an $\epsilon_{max}$ 2.45×10$^4$. Elemental analysis for C$_{22}$H$_{28}$Cl$_1$N$_3$O$_3$ (M.W. 417.9): Calcd. C, 63.23; H, 6.75; N, 10.05. Found: C, 63.41; H, 6.80; N, 10.05.

Properties of UV Absorbers of the Present Invention

Physical properties, including optical absorption profiles were measured for various of the compounds of the present invention, as illustrated in Tables 1 and 2 below. In Table 1, $\lambda_{max}$ is the wavelength of maximum absorption (measured in MeOH as indicated in the Table, $\epsilon_{max}$ is the extinction coefficient, and the half bandwidth is the width of the absorption peak centered about $\lambda_{max}$ as measured at one-half the maximum absorption at $\lambda_{max}$, all of the foregoing measured in methanol. "%Yield" represents the yield of compound using the method to make it described above.

TABLE 1

| Comp. No. | $R_1$ | $R_2$ | $R_3$ | % Yield | $\lambda_{max}^{(nm)}$ (in MeOH) | $\varepsilon_{max}^{(\times 10^4)}$ | Half Band-width (nm) | Melting Point (°C.) |
|---|---|---|---|---|---|---|---|---|
| VIII-A | H | H | H | 65 | 338 | 2.34 | 56 | 72–73 |
| VIII-B | H | Me | H | 60 | 340 | 2.52 | 54 | 48–50 |
| VIII-C | H | MeO | H | 72 | 346 | 2.60 | 52 | 52–53 |
| VIII-D | H | Cl | H | 70 | 346 | 2.45 | 57 | 81–82 |
| VIII-E | H | H | Cl | 73 | 343 | 2.21 | 54 | 60–62 |

It will be seen from Table 1 that each of the inventive compounds of formula (VIII) had a $\lambda_{max}$ in the desirable 330–350 nm range, had a narrow half bandwidth (50–60 nm) indicating a desirable sharp drop off in absorption at wavelengths in the 390–400 nm range, and high extinction coefficients (greater than $2 \times 10^4$). Further advantages of compounds of Formula (VIII) are described under the "Photographic Evaluation" section below. For example, as shown under the section "Photographic Evaluation", in Table 3, although the compound VIII-A (which has the asymmetric carbon (a racemic carbon center) as required by the present invention) in Table 1 is a solid compound, it did not crystallize out during photographic evaluation either in cold dispersion or in the coating.

Physical properties of formula (XIII) compounds of the present invention and yields from the methods described above, are listed below in Table 2:

TABLE 2

| Comp. No. | $R_1$ | $R_2$ | $R_3$ | $R_{10}$ | $R_{11}$ | $R_{12}$ | $R_{13}$ | % Yield | M.P. (°C.) or Liquid |
|---|---|---|---|---|---|---|---|---|---|
| XIII-A | H | H | H | H | Ethyl | n-Butyl | Acetyl | 99 | Liquid |
| XIII-B | H | H | H | H | Ethyl | n-Butyl | 2-Ethyl hexanoyl | 92 | Liquid |
| XIII-C | H | H | H | H | Ethyl | n-Butyl | 2-Methyl butanoyl | 87 | Liquid |
| XIII-D | H | H | H | H | Ethyl | n-Butyl | Acryloyl | 45* | Liquid |
| XIII-E | H | Cl | H | H | Ethyl | n-Butyl | 2-Ethyl hexanoyl | 90 | Liquid |
| XIII-F | H | Cl | H | H | Ethyl | n-Butyl | Acetyl | 99 | 42–45 |
| XIII-G | H | Cl | H | H | Ethyl | n-Butyl | 2-Methyl butanoyl | 94 | Liquid |
| XIII-H | H | H | Cl | H | Ethyl | n-Butyl | Acetyl | 84 | Liquid |
| XIII-I | H | H | Cl | H | Ethyl | n-Butyl | 2-Ethyl hexanoyl | 95 | Liquid |

*Low yield due to thermally induced polymerization.

5-Chloro- or 5'-chloro-substituted UV dyes (compounds VIII-E and VIII-D) particularly appear to offer an appropriate hue and a sharper batho-cut (that is, steeper slope at longer wavelengths of absorption) as shown in FIG. 1 when compared with the comparative (a combination of comparative compounds V-A and V-B). Furthermore, the chloro or fluoro substituted compounds of formula (VIII) of the present invention are generally more light stable.

Photographic Evaluation 1.45 g of UV absorber was dissolved at elevated temperature (50°–70° C.) in 480 mg of 1,4-cyclohexylenedimethylene bis (2-ethylhexanoate) and, if UV absorber was a solid at room temperature, an additional 4.35 g of ethyl acetate was used. This oil phase was added with high shear stirring to a 70° C. aqueous gelatin solution (containing per liter 40.1 g of gelatin and 31.0 mL of 10% aqueous Alkanol - XC) and passed five times through a colloid mill for adequate particle size reduction. The dispersion is inspected microscopically for general particle size and crystallinity, and coated at $1.16 \times 10^{-4}$ moles/ft$^2$ on an acetate base in a two layer SOC-type format, allowed to dry and the coating is also inspected microscopically for crystallinity (See Table 3). Fresh coated spectral absorption data are recorded using a Perkin-Elmer Lambda 4C High Performance UV-VIS Spectrophotometer, and coated samples are HID (50 Klux Daylight; 315–700 nm) and HIS (50 Klux Sunshine; 280–700 nm) tested and compared to fresh data in order to obtain UV absorber intrinsic light stability information. (For HID and HIS explanation, see Lewis R. Koller, Ultraviolet Radiation, John Wiley & Sons, Inc., N.Y., N.Y., 1965).

Absorption spectra for various of the compounds were obtained in solution and in coating as described below and are shown in FIGS. 1–3. In particular, FIG. 1 shows the absorption spectra in solution for a mixture of comparative compounds V-A and V-B (solid line), as well as for the inventive compound VIII-E (dashed line) and the inventive compound VIII-D (dotted line). FIG. 2 shows the absorption spectra (in coating) for inventive compound VIII-A in total transmission mode. FIG. 3 shows the absorption spectra (in coating) for comparative compound VIII-A in specular mode. Note from FIG. 1 that inventive UV absorbing compounds VIII-D and VIII-E have about the same absorbance as a commonly used mixture of comparative UV absorbing compounds V-A/V-B in the important region of about 330–370 nm. However, inventive compounds VIII-D and VIII-E both have steeper slopes at their longer wavelengths of absorption (that is, near 380 nm) and particularly drop to a lower absorption at their longest wavelength of absorption, than does the mixture of V-A/V-B. Note from FIGS. 2 and 3 that inventive UV absorbing compound VIII-A exhibits a far higher extinction coefficient than comparative control compounds V-A and V-B in both modes of operation.

Microscopic observations for crystallanity in experimental UV absorber dispersions and coatings of these materials and their absorption spectra were performed as described here. Microscopy is undertaken in the preparation of dispersions of experimental materials in order to provide an initial indication of physical properties such as general particle size and stability (that is, tendency to crystallize). The microscopic particle size characterizations are normally performed using oil immersion optics (~1000×) microscopy, and cross-polarized (~200×) microscopy is used for crystal characterization. Microscopic evaluation of the coatings is also undertaken as a dispersion may recrystallize in the coated format. Assuming there are no re-crystallization problems, duplicate samples are spectrophotometrically measured using a Perkin-Elmer High Performance Lambda 4C spectrometer. These samples are then submitted for 2 weeks (or 4 weeks) HID and HIS light stability testing, and the post-testing spectra is measured and compared to the fresh measurements in order to determine intrinsic light stability of the UV absorber. Since the experimental dispersion formulation used for these experiments is common and only optimized from the standpoint of low melting solids and its beneficial effect on dispersion crystallinity, coated spectroscopy data are obtained primarily using the total transmission mode of operation where an integrating sphere is used in the spectrophotometer. This has the effect of diminishing light scattering effects due to particle size, so misleading extinction differences caused by light scattering in the specular mode can be overlooked.

A microscopic check for crystal formation from the above procedure, yielded the results shown in Table 3 below. This table further illustrates that even the comparative compound XII (an exact match to Compound VIII-A in terms of number of carbon atoms) lacking the extra racemic carbon center did crystallize out in the coating.

TABLE 3

Tendency to Form Undesirable Crystals

| Sample ID | Dispersion | Coating |
|---|---|---|
| Comparative Comp. No. IX | Crystallized | Crystallized |
| Comparative Comp. No. X | Crystallized | Crystallized |
| Comparative Comp. No. XI | Crystallized | Crystallized |
| Comparative Comp. No. XII | It did not crystallize | Crystallized |
| Inventive Comp. No. VIII-A | It did not crystallize | It did not crystallize |
| Inventive Comp. No. VIII-B | It did not crystallize | It did not crystallize. |
| Inventive Comp. No. VIII-C | It did not crystallize | It did not crystallize |

Intrinsic light stability data for inventive UV absorber dyes are summarized in Tables 4 and 5. A mixture of the known UV absorbers V-A & V-B has been used as a Control in each coating set. The optical density loss, relative to the control coatings, was measured at 350 nm from coating spectral data.

The comparative liquid UV dye Compound No. III from European Patent Application EP 0 451 813, was prepared to show the advantage of superior intrinsic light stability of inventive UV dyes over the Compound No. III. Comparative compound III has just one ether linkage although it contains a racemic carbon bearing alkyl group. The inventive UV dye compounds of Table 1 bear an additional ether linkage and an additional racemic carbon center. It is clear from Table 4 that the inventive UV dye compounds have greater intrinsic light stability compared to the known Compound III. The 5-chloro-substituted analog VIII-D of the present invention (Table 1) exhibits intrinsic light stability similar to the control and the inventive compound XVI (see above) appears to be even better than the control in 2 week HID test and similar in 2 week HIS test. Thus, the inventive compounds have good light stability which is better than that of comparative compound III.

TABLE 4

Light Stability

| Sample ID. | 2 Week HID | 2 Week HIS |
|---|---|---|
| Compound No. III (Comparative) | −2.9x | −4.4x |
| Compound No. VIII-A (Inventive) | −1.2x | −0.7x |
| Compound No. VIII-C (Inventive) | −1.4x | −2.7x |
| Compound No. VIII-D (Inventive) | −1.2x | −1.0x |
| Compound No. XVI (Inventive) | 0 | −1.2x |

NOTE:
X represents the ratio with respect to comparative control compounds V-A and V-B Inventive compounds VIII-D & VIII-E (Table 1) were found to be more soluble in tris (methyl phenyl)phosphoric acid ester in order to improve the dispersibility. This solvent was no longer necessary when the compound VIII-D (Table 1) was converted to XIII-E, XIII-F, and XIII-G (Table 2) and the compound VIII-E converted to XIII-H and XIII-I by introducing an additional racemic carbon center or eliminating hydrogen-bonding caused by the secondary alcoholic group.

TABLE 5

| | Light Stability | | | |
|---|---|---|---|---|
| Sample ID | 2 Week HID | 2 Week HIS | 4 Week HID | 4 Week HIS |
| III, Comparative | −2.9x | −4.4x | — | — |
| XIII-E, Inventive | −0.4x | 0 | −0.5x | −0.5x |
| XIII-F, Inventive | −0.5x | −0.1x | −0.7x | −0.8x |
| XIII-G, Inventive | −0.4x | 0 | −0.7x | −0.7x |
| XIII-H, Inventive | −0.2x | −0.1x | −0.4x | −0.3x |
| XIII-I, Inventive | −0.7x | 0 | −0.6x | −0.2x |
| XIV, Inventive | 0 | 0 | −0.6x | −0.5x |
| XV, Inventive | −0.3x | −0.2x | −0.5x | −0.2x |

NOTE:
x represents the ratio with respect to comparative control compounds V-A and V-B.

The preceding examples are set forth to illustrate specific embodiments of this invention and are not intended to limit the scope of the compositions or materials of the invention. It will be understood that variations and modifications can be effected within the spirit and scope of the invention.

We claim:

1. A photographic element comprising an ultraviolet absorbing compound of the following structure:

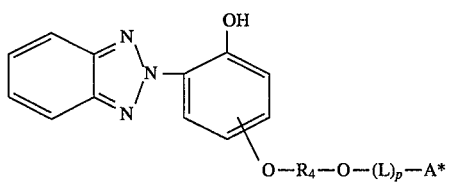

wherein:

R₄ is a bivalent linking group in which the atoms of the chain extending between the two oxygen atoms shown are all saturated; the benzo or phenyl ring shown may be further substituted or unsubstituted;

L is a bivalent linking group;

p is 0 or 1;

A* is an alkyl group having an asymmetric carbon or asymmetric silicon atom, and;

wherein the ultraviolet absorbing compound of formula (I) is a mixture of two enantiomers about the asymmetric carbon or asymmetric silicon of A*.

2. A photographic element according to claim 1 wherein the ultraviolet absorbing compound of formula (I) has the following structure:

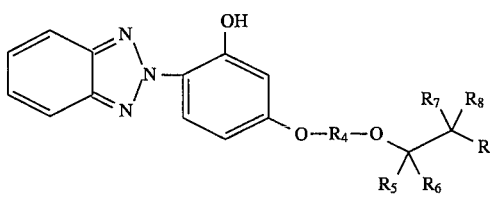

3. A photographic element according to claim 2 wherein p is 1 and L is an alkylene group having a chain extending between the O shown and A* of 1 to 4 carbon atoms in length.

4. A photographic element according to claim 2 wherein the ultraviolet absorbing compound is a 60/40 to 40/60 mixture of two enantiomers.

5. A photographic element according to claim 2 wherein the ultraviolet absorbing compound of formula (I) is of formula (IA):

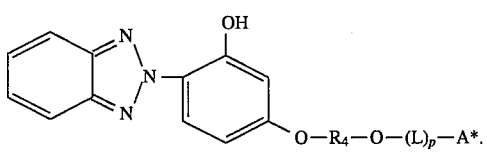

wherein:

R₄ is a bivalent linking group in which the atoms of the chain extending between the two oxygen atoms shown are all saturated;

R₅ and R₆, together with the carbon atom to which they are attached, forms a carbonyl group or they are, independently, H or substituents, and the benzo or phenyl ring shown may be further substituted or unsubstituted;

R₇, R₈ and R₉ are, independently: H; halogen; cyano; a 1 to 18 carbon alkyl group or alkoxy group either of which may have 1 to 5 intervening oxygen, sulfur or nitrogen atoms; 6 to 20 carbon aryl group or aryloxy group; or a heteroaromatic group in which the aromatic ring has 1 to 3 heteroatoms selected from N, S and O;

provided that R₇, R₈, and R₉ are selected such that the carbon atom to which they are attached is asymmetric;

the ultraviolet absorbing compound of formula (IA) being a 60/40 to 40/60 mixture of two enantiomers.

6. A photographic element according to claim 5 wherein R₄ is an alkylene group having a chain of 2 to 20 atoms in length, with or without intervening oxygen, sulfur or nitrogen atoms, and the benzo or phenyl ring shown may be further substituted or unsubstituted.

7. A photographic element according to claim 2 wherein the ultraviolet absorbing compound of formula (I) is of formula (IA):

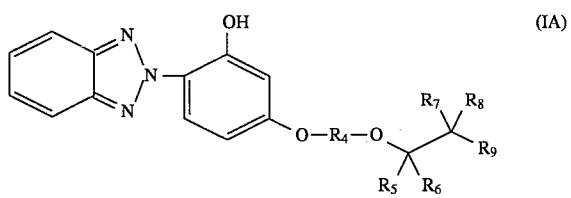

wherein:

R₄ is a bivalent linking group in which the atoms of the chain extending between the two oxygen atoms shown are all saturated;

R₅ and R₆, together with the carbon atom to which they are attached, forms a carbonyl group or they are, independently, H or substituents, and the benzo or phenyl ring shown may be further substituted or unsubstituted;

R₇, R₈ and R₉ are, independently H or an alkyl group, provided that they are selected such that the carbon atom to which they are attached is asymmetric;

the ultraviolet absorbing compound of formula (IA) being a 60/40 to 40/60 mixture of two enantiomers.

8. A photographic element according to claim 7 wherein R₄ is an alkylene group having a chain of 2 to 20 atoms in length, with or without intervening oxygen, sulfur or nitrogen atoms, and the benzo or phenyl ring shown may be further substituted or unsubstituted.

9. A photographic element according to claim 2, the element additionally comprising at least one light sensitive silver halide emulsion layer and a non-light sensitive layer, wherein the ultraviolet absorbing compound is located in the non-light sensitive layer.

10. A photographic element according to claim 9 wherein the non-light sensitive layer containing the ultraviolet absorbing compound is located above all light sensitive layers.

11. A photographic element according to claim 1, additionally comprising a reflective support and at least one silver halide emulsion layer, and wherein the ultraviolet absorbing compound is located in the silver halide emulsion layer or in a layer positioned further from the support than the silver halide emulsion layer.

12. A photographic element according to claim 11 additionally comprising a fluorescent brightener.

13. A photographic element according to claim 12 wherein the fluorescent brightener absorbs ultraviolet in the 350–410 nm range in order to fluoresce in the range of 400–500 nm.

14. A photographic element according to claim 1 wherein the ultraviolet absorbing compound is present in an amount of between 0.2 g/m² to 10 g/m².

15. A photographic element comprising a light-sensitive silver halide emulsion layer and an ultraviolet absorbing compound present in the light-sensitive layer or another layer of the element, the ultraviolet absorbing compound having the formula (Ia):

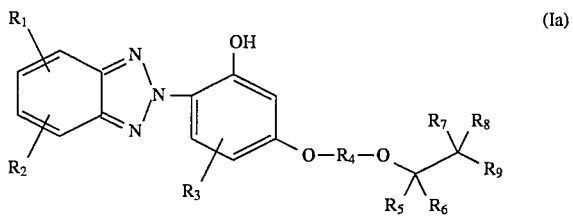

R$_1$, R$_2$ and R$_3$ independently represent alkyl group, alkoxy group, aryl group, heteroaryl group, or aryloxy group, and the alkyl or alkoxy may contain from 1 to 5 intervening oxygen, sulfur or nitrogen atoms, or may contain double bonds, or any of R$_1$, R$_2$ or R$_3$ is H, cyano or a halogen atom, or both R$_1$ and R$_2$ together form an aromatic group or hetero aromatic group;

R$_4$ is a bivalent linking group in which the atoms of the chain extending between the two oxygen atoms shown are all saturated;

R$_5$ and R$_6$, together with the carbon atom to which they are attached, forms a carbonyl group or they are, independently, H or substituents; and R$_7$, R$_8$ and R$_9$ are, independently H or an alkyl group provided that they are selected such that the carbon atom to which they are attached is asymmetric;

the ultraviolet absorbing compound of formula (Ia) being a 60/40 to 40/60 mixture of two enantiomers.

16. A photographic element according to claim 15 wherein R$_4$ is an alkylene group having a chain of 2 to 20 atoms in length, with or without intervening oxygen, sulfur or nitrogen atoms.

17. A photographic element according to claim 15 wherein R$_4$ is an alkylene chain of 2 to 6 atoms in length with no intervening heteroatoms.

18. A photographic element according to claim 16 wherein R$_4$ is an alkylene chain as described with an ether or ester containing substituent.

19. A photographic element according to claim 18 wherein the ether or ester containing substituent in R$_4$ is of the formula R$_{10}$—O—(R$_{11}$)$_n$— or R$_{10}$C(O)O—(R$_{11}$)$_n$—, where R$_{10}$ and R$_{11}$ are, independently, an alkyl group and n is 0 or 1.

20. A photographic element according to claim 15 where R$_7$, R$_8$ and R$_9$ are a 1 to 20 carbon alkyl group, or H.

21. A photogaphic element according to claim 15 wherein R$_5$ and R$_6$ form a carbonyl group with the carbon to which they are attached, or represent an alkyl group or H.

22. A photographic element according to claim 15 wherein each of R$_1$, R$_2$ and R$_3$, is alkyl, alkoxy, H or halogen.

23. A photographic element according to claim 15 wherein each of R$_1$, R$_2$ and R$_3$ is alkyl, H or halogen.

24. A photographic element according to claim 2 wherein R$_4$ contains an asymmetric carbon atom.

25. A photographic element according to claim 2 wherein the ultraviolet absorbing compound of formula (I) is a 50/50 mixture of two enantiomers.

26. A photographic element according to claim 15 wherein the ultraviolet absorbing compound of formula (Ia) is a 50/50 mixture of two enantiomers.

27. An ulatraviolet absorbing compound of the following structure:

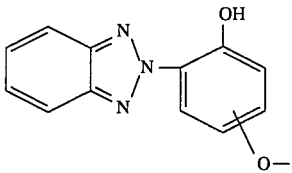

wherein:

R$_4$ is a bivalent linking group in which the atoms of the chain extending between the two oxygen atoms shown are all saturated; the benzo or phenyl ring shown may be further substituted or unsubstituted;

L is a bivalent linking group;

p is 0 or 1;

A* is an alkyl group having an asymmetric carbon or asymmetric silicon atom, and;

wherein the ultraviolet absorbing compound of formula (I) is a mixture of two enantiomers about the asymmetric carbon or asymmetric silicon of A*.

28. An ultraviolet absorbing compound according to claim 27, wherein the compound is of formula (IA):

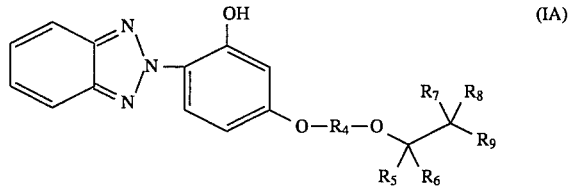

wherein:

the benzo and phenyl rings shown are further unsubstituted or substituted with: a 1 to 18 carbon alkyl or alkoxy either of which may have 1 to 5 intervening oxygen, sulfur or nitrogen atoms; 6 to 20 carbon aryl, heteroaryl in which an aromatic ring has 1 to 3 heteroatoms selected from N, S and O; or aryloxy; or any of the foregoing substituted with 1 to 17 carbon alkyl or alkoxy, 1 to 17 carbon alkyl sulfide, 0 to 17 carbon amino, halogen, or cyano;

R$_4$ is a bivalent linking group in which the atoms of the chain extending between the two oxygen atoms shown are all saturated; and R$_5$ and R$_6$, together with the carbon atom to which they are attached, forms a carbonyl group or they are, independently: H; halogen; cyano; a 1 to 18 carbon alkyl or alkoxy either of which may have 1 to 5 intervening oxygen, sulfur or nitrogen atoms; 6 to 20 carbon aryl or aryloxy; heteroaryl in which an aromatic ring has 1 to 3 heteroatoms selected from N, S and O; or any of the foregoing substituted with 1 to 17 carbon alkyl or alkoxy, 1 to 17 carbon alkyl sulfide, 0 to 17 carbon amino, halogen, or cyano;

R$_7$, R$_8$ and R$_9$ are, independently: H; halogen; cyano; a 1 to 18 carbon alkyl or alkoxy either of which may have 1 to 5 intervening oxygen, sulfur or nitrogen atoms; 6 to 20 carbon aryl or aryloxy; heteroaryl in which an aromatic ring has 1 to 3 heteroatoms selected from N, S and O; or any of the foregoing substituted with 1 to 17 carbon alkyl or alkoxy, 1 to 17 carbon alkyl sulfide, 0 to 17 carbon amino, halogen, or cyano;

provided that R$_7$, R$_8$, and R$_9$ are selected such that the carbon atom to which they are attached is asymmetric;

the ultraviolet absorbing compound of formula (IA) being a 60/40 to 40/60 mixture of two enantiomers.

29. An ultraviolet absorbing compound according to claim 28, having the formula (Ia):

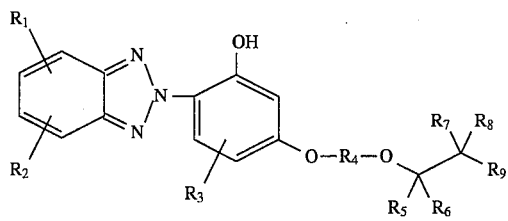

wherein:

$R_1$, $R_2$ and $R_3$ are, independently: a 1 to 18 carbon alkyl or alkoxy either of which may have 1 to 5 intervening oxygen, sulfur or nitrogen atoms; 6 to 20 carbon aryl, heteroaryl in which an aromatic ring has 1 to 3 heteroatoms selected from N, S and O; or aryloxy; or any of the foregoing substituted with 1 to 17 carbon alkyl or alkoxy, 1 to 17 carbon alkyl sulfide, 0 to 17 carbon amino, halogen, or cyano.

* * * * *